US006965026B2

(12) United States Patent
Zaworotko et al.

(10) Patent No.: US 6,965,026 B2
(45) Date of Patent: Nov. 15, 2005

(54) NANOSCALE FACETED POLYHEDRA

(75) Inventors: Michael J. Zaworotko, Tampa, FL (US); Brian Moulton, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 342 days.

(21) Appl. No.: 10/083,781

(22) Filed: Feb. 25, 2002

(65) Prior Publication Data

US 2002/0120165 A1 Aug. 29, 2002

Related U.S. Application Data

(60) Provisional application No. 60/314,855, filed on Aug. 24, 2001, and provisional application No. 60/270,998, filed on Feb. 23, 2001.

(51) Int. Cl.$^7$ .............................. C07F 1/08; C07F 3/06; C07C 39/00; C07C 51/00; B01D 9/00
(52) U.S. Cl. ................................ 536/119; 977/DIG. 1; 560/119
(58) Field of Search .......................... 536/119; 560/119; 977/DIG. 1

(56) References Cited

U.S. PATENT DOCUMENTS

| | | | |
|---|---|---|---|
| 4,310,440 A | 1/1982 | Wilson et al. | |
| 4,440,871 A | 4/1984 | Lok et al. | |
| 4,454,153 A | 6/1984 | Lowicki et al. | |
| 4,500,651 A | 2/1985 | Lok et al. | |
| 4,880,761 A | 11/1989 | Bedard et al. | |
| 5,648,508 A | 7/1997 | Yaghi | |
| 6,072,044 A * | 6/2000 | Seeman et al. | 536/22.1 |
| 6,180,024 B1 | 1/2001 | Blackwood et al. | |
| 6,187,440 B1 | 2/2001 | Wu | |
| 6,531,107 B1 * | 3/2003 | Spencer et al. | 423/276 |

FOREIGN PATENT DOCUMENTS

WO   WO 99/05151 A1   2/1999

OTHER PUBLICATIONS

Stowell et al, "Self–Assembled Honeycomb Networks of Gold Nanaocrystals", Nano Letters , 2001, vol. 1, No. 11, pp. 595–600.*
Holleman, A.F. et al. "Lehrbuch der Anorganischen Chemie 101.Auflage" (English translation) 1995,.
Abourahma, H. et al. "Hydroxylated nanoballs: synthesis, crystal structure, solubility and crystallization on surfaces" *Chem. Commun.*, 2001, 2380–2381.
Bourne, S.A. et al. "Self–assembly of nanometer–scale secondary building units into an undulating two–dimensional network with two types of hydrophobic cavity" *Angew. Chem. Int. Ed.*, Jun. 2001, 40(11):2111–2113.
Jotham, R.W. et al. "Antiferromagnetism in transition–metal complexes. Part IV. Low–lying excited states of binuclear copper (II) carboxylate complexes" *Dalton Trans.*, 1972, pp. 428–438.
Kato, M. et al. "Copper(II) complexes with subnormal magnetic moments" *Chem. Rev.*, 1964, 64(2):99–128.
Lu, J. et al. "Polygons and faceted polyhedra and nanoporous networks" *Angew. Chem. Int. Ed.*, 2001, 40(11):2113–2116.
Moulton, B. et al. "Nanoballs: nanoscale faceted polyhedra with large windows and cavities" *Chem. Commun.*, 2001, 863–864.
Moulton, B. and M. Zaworotko "From molecules to crystal engineering: supramolecular isomerism and polymorphism in network solids" *Chem. Rev.*, Jun. 2001, 101(6):1629–1658.
Sun, S.H. et al. "Monodisperse FePt Nanoparticles and Ferromagnetic FePt Nanocrystal Superlattices" *Science*, Mar. 17, 2000, 287:1989–1992.
Tamura, H. et al. "Semiconductor Ferromagnetism in Quantum Dot Array" *Phys. Status Solidi B.*, Mar. 19, 2001, 224(3):723–725.
Yaghi, O.M. et al. "Synthetic strategies, structure patterns, and emerging properties in the chemistry of modular porous solids" *Acc. Chem. Res.*, 1996, 31(8):474–484.
Zhang, X.X. et al. "Cooperative magnetic behavior in the coordination polymers [Cu$_3$(TMA)$_2$L$_3$] (L = H$_2$O, pyridine)" *J. Appl. Phys.*, May 1, 2000, 87(9):6007–6009.
Bourne, S.A. et al. "1–D coordination polymers containing benzenedicarboxylate" *Crystal Engineering*, 2001, 4:25–36.
Chui, S. et al. "A Chemically Functionalizable Nanoporous Material [Cu$_3$(TMA)$_2$(H$_2$O)$_3$]$_n$," *Science*, Feb. 19, 1999, 283:1148–1150.
Yaghi, O.M. et al. "Crystal Growth of Extended Solids by Nanaqueous Gel Diffusion" *Chem. Mater.*, 1997, 1074–1076.
Bourne, S.A. et al. "Coexisting covalent and noncovalent nets: parallel interpenetration of a puckered rectangular coordination polymer and aromatic noncovalent nets" *Chem Commun.*, 2001, 9:861–862.
Wu, C–D. et al. "Hydrothermal synthesis of two new zinc coordination polymers with mixed ligands" *Inorganic Chemistry Communications*, 2001, 4:561–564.

(Continued)

Primary Examiner—Nathan M. Nutter
(74) Attorney, Agent, or Firm—Saliwanchik, Lloyd & Saliwanchik

(57) ABSTRACT

The subject invention pertains to nanoscale polyhedron-shaped molecules having molecular building blocks connected at their vertices. The subject invention also concerns methods of producing nanoscale polyhedrons utilizing a self-assembly reaction. The resultant molecules are faceted polyhedra that are porous, chemically robust, contain chemically accessible sites on their facets, and which are neutral and soluble in common laboratory solvents. The nanoscale polyhedrons can exhibit additional desirable physical properties, such as ferromagnetic properties.

29 Claims, 30 Drawing Sheets

(19 of 30 Drawing Sheet(s) Filed in Color)

OTHER PUBLICATIONS

Shi, Q et al. "Solvothermal syntheses and crystal structures of two metal coordination polymers with double–chain structures" *Polyhedron*, 2001, 20:3287–3293.

Plater, M.J. et al. "Synthesis and characterization of polymeric manganese and zinc 5–hydroxyisophthalates" *Polyhedron*, 2001, 20:2293–2303.

Oshio, H. and H. Ichida "Control of Intramolecular Magnetic Interaction by the Spin Polarization of $d_\pi$ Spin to $p_\pi$ Orbital of an Organic Bridging Ligand" *J. Phys. Chem.*, 1995, 99:3294–3302.

Holleman, A.F. et al. "Lehrbuch der Anorganischen Chemie 101.Auflage"no date.

Kepert, C.J. and M.J. Rosseinsky "A porous chiral framework of coordinated 1,3,5–benzenetricarboxylate: quadruple interpenetration of the (10,3)–a network" *Chem. Commun.*, 1998, 1:31–32.

Yaghi, O.M. et al. "Construction of Porous Solids from Hydrogen–Bonded Metal Complexes of 1,3,5–Benzenetricarboxylic Acid" *J. Am. Chem. Soc.*, 1996, 118:9096–9101.

Yaghi, O.M. et al. "Selective binding and removal of guests in a microporous metal–organic framework" *Nature*, Dec. 14, 1995, 378:703–706.

\* cited by examiner n = 9, 11, 15, 18 n = 17  FIG. 2T

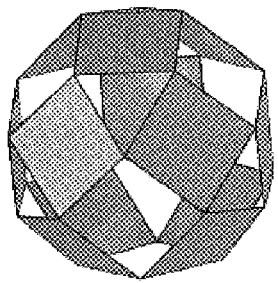 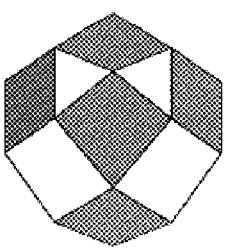 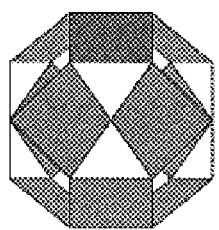 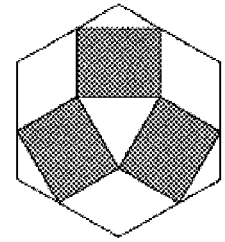
FIG. 6A   FIG. 6B   FIG. 6C   FIG. 6D
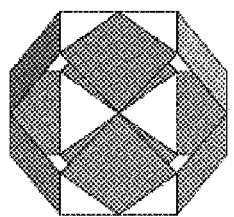 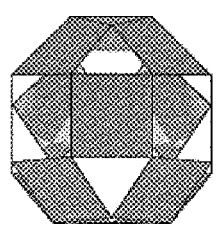 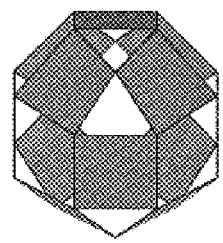
FIG. 6E   FIG. 6F   FIG. 6G
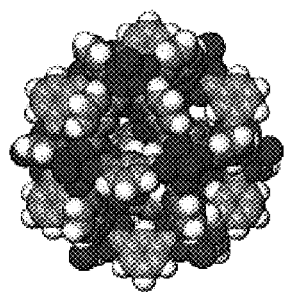 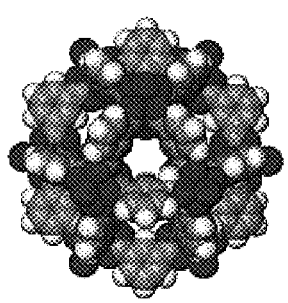 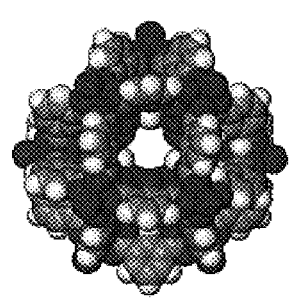
FIG. 6H   FIG. 6I   FIG. 6J Actually 72°, but can sustain distortion to 90° (proven by molecular modelling experiments)

NANOSCALE FACETED POLYHEDRA

CROSS-REFERENCE TO RELATED APPLICATIONS

This application claims the benefit of provisional patent application Ser. No. 60/270,998, filed Feb. 23, 2001, and provisional patent application Ser. No. 60/314,855, filed Aug. 24, 2001.

The subject invention was made with government support under a research project supported by National Science Foundation Grant No. DMR-0101641. The government has certain rights in this invention.

BACKGROUND OF THE INVENTION

Design principles that are based upon the concepts of crystal engineering and self-assembly have recently afforded new classes of crystalline solids that possess important physical properties such as bulk magnetism or porosity. Large-scale molecular networks have been developed to encapsulate other materials and these are playing an ever-increasing role in the pharmaceutical industry and as materials for sensors, and liquid crystals. In addition, with the inclusion of metals within the structures, the large polymers formed by these crystals have magnetic properties as well as exhibiting catalytic properties.

In recent years, chemists have developed synthetic design strategies that are based on the concept of self-assembly. This supramolecular approach to synthesis has afforded a new generation of discrete, high molecular weight compounds. These compounds are exemplified by nanoscale spheroid architectures that are based upon Platonic, or regular, and Archimedean, or semi-regular, solids. Nanoscale versions of Platonic and Archimedean solids have been prepared wherein their building blocks, molecular polygons, are connected at their edges. Closed convex polyhedra are generated in this manner.

In contrast to the Platonic and Archimedean solids that have been generated by edge-sharing of molecular polygons, it would be advantageous to produce open-shell polyhedra, which would necessarily be porous in a predictable manner, and thus be susceptible to a high degree of control over structure and functionality.

BRIEF SUMMARY OF THE INVENTION

The subject invention pertains to molecular polyhedra constructed of molecular building blocks that approximate polygons (hereinafter molecular polygons), in which the molecular polygons are linked at their vertices. The molecular polygons can comprise metal-organic moieties (also termed nanoscale secondary building units, or nSBUs) or non-metal-organic moieties. The molecular polyhedra of the subject invention provide several advantages over nanoscale solids that are based on conventional Platonic (regular) and Archimedean structures, which are constructed of building blocks linked at their edges.

The molecular polyhedra and polymeric structures of the subject invention can be constructed of molecular polygons (such as triangles, squares, and other polygons), wherein the molecular polygons are linked at their vertices by a linking molecular moiety that subtends the appropriate angle between the planes of the linked molecular polygons. By virtue of the vertex-linkages between their component polygons, the molecular polyhedra of the subject invention can have open faces (faceted polyhedra), and can therefore exhibit desirable physical properties, such as porosity. nSBU vertices can be linked via covalent interactions using the coordinating ligands exemplified herein, such as bifunctional or trifunctional carboxylates, as well as other appropriate coordinating ligands. Appropriate coordinating ligands include those angular multifunctional ligands capable of sustaining the desired dihedral angle(s) between nSBUs. Molecular polygons comprising non-metal-organic moieties can be liked at their vertices via non-covalent interactions through bridging ligands. Appropriate bridging ligands include those angular ligands capable of sustaining the desired dehedral angle(s) between non-metal polygons. nSBUs vertices can be liked to vertices of non-metal polygons through bridging ligands, using non-covalent interactions. The appropriate bridging ligands include those angular ligands capable of sustaining the desired dihedral angle(s) between the metal polygon and the non-metal polygon. Preferably, the bridging ligand is a multifunctional molecular moiety capable of sustaining multiple supramolecular interaction.

The subject invention further pertains to compounds comprising the molecular polyhedra described herein. The molecular polyhedra can be utilized to generate a wide variety of compositions in an efficient and predictable manner.

The molecular polygons used to construct the polyhedra of the subject invention are preferably, but not limited to, metal-organic moieties (nSBUs). Advantages inherent in the utilization of nSBUs include: (i) metal-organic coordination polymers can be prepared via self-assembly, allowing inexpensive synthesis, often with one step and high yield (e.g., "one pot" reactions); structures having metal-organic building blocks are inherently modular since they contain at least two components, a node (such as an nSBU) and a "spacer" (such as a multifunctional organic coordinating ligand); structures having metal-organic building blocks can have an open framework, which conveys the ability to gain very precise control over cavities and channels; metal organic coordination polymers are typically of low solubility and, therefore, kinetic and thermodynamic products can be formed for a particular set of components, making them useful for sorption from, and to, solution phases; and metal-organic incorporating structures tend to be moderately thermally stable and air and water stable (many compounds of the subject invention are stable to 200° C. and others are stable at or above 400° C.). In addition, the use of metal-organic building blocks are particularly useful for the construction of molecular polyhedra (and compounds comprising such molecular polyhedra) that can exhibit one or more advantageous properties, such as magnetic activity, luminescent activity, phosphorescent activity, fluorescent activity, and catalytic and redox activity.

The subject invention also concerns methods of producing polyhedron-shaped molecules with polygons, such as metal-organic polygons, or non-metal-organic polygons, linked at their vertices. The methods of the subject invention can involve as little as one self-assembly reaction, where inexpensive, commercially available reagents can be utilized.

Examples of general formulas for polyhedron molecules and polymeric structures of the subject invention that are constructed from metal-organic polygons (nSBUs) include:

Formula 1: $(MA)_{12}$

Formula 1 represents a general formula for molecules of the subject invention having a spheroid architecture (e.g., nanoballs) (90°) of the subject invention, wherein M can be any metal that can sustain 4-fold rotational symmetry, A is a bifunctional carboxylate that subtends an angle of 90° (allowing for geometric distortion), and wherein any coordinating ligand or solvent molecule may optionally be coordinated to each M.

Examples of bifunctional carboxylates that can subtend an angle of 90° are shown in FIGS. 24A–24C. The angle subtended by the bifunctional carboxylate in FIG. 24B is actually 72°, but can sustain distortion to 90°, as determined by molecular modeling experiments.

Formula 2: $(MA)_{24}$

Formula 2 represents a general formula for nanoballs (120°) of the subject invention, wherein M can be any metal that can sustain 4-fold rotational symmetry, wherein A is a bifunctional carboxylate that subtends an angle of 120° (allowing for geometric distortion), and wherein any coordinating ligand or solvent molecule may optionally be coordinated to each M.

Formula 3: $(MA)_{60}$

Formula 3 represents a general formula for nanoballs (144°) of the subject invention, wherein M can be any metal that can sustain 4-fold rotational symmetry, wherein A is a bifunctional carboxylate that subtends an angle of 144° (allowing for geometric distortion), and wherein any coordinating ligand or solvent molecule may optionally be coordinated to each M.

Formula 4: $(MA)_n$

Formula 4 represents a general formula for a square (tetragonal) 2D network or lattice of the subject invention, wherein M can be any metal that can sustain 4-fold rotational symmetry, A is a bifunctional carboxylate that subtends an angle greater than 90°, and preferably subtends an angle of 120°, allowing for geometric distortion, wherein 'n' indicates a polymeric structure, albeit in two dimensions (i.e., $n \geq 4$), and wherein any coordinating ligand or solvent molecule may optionally be coordinated to each M.

Formula 5: $(MA)_n$

Formula 5 represents a general formula for hexagonal (Kagomé) 2D network or lattice of the subject,invention, wherein M can be any metal that can sustain 4-fold rotational symmetry, wherein A is a bifunctional carboxylate that subtends an angle greater than 90°, and preferably subtends an angle of 120°, allowing for geometric distortion, wherein 'n' indicates a polymeric structure, albeit in two dimensions (i.e., $n \geq 3$), and wherein any coordinating ligand or solvent molecule may optionally be coordinated to each M.

Formula 6: $(M^1{}_4 M^2{}_3 A_3 Y_2)_n$

Formula 6 represents a general formula for an embodiment of a polymer of the subject invention, as shown in FIGS. 11A–11F, wherein $M^1$ can be any metal that can sustain 3-fold rotational symmetry, wherein $M^2$ can be any metal that can sustain 4-fold rotational symmetry, wherein A is a trifunctional carboxylate with 3-fold rotational symmetry (allowing for geometric distortion), wherein Y is any −1 anion ("$Y_2$" could also be just one "Y", if Y is a −2 anion), wherein 'n' indicates a polymeric structure in three dimensions (i.e., $n \geq 2$), and wherein any coordinating ligand or solvent molecule is optionally coordinated to each M.

Formula 7: $(M_3 A_2)_n$

Formula 7 represents a general formula for another embodiment of a polymer of the subject invention, as shown in FIGS. 15A–15F, wherein M can be any metal that can sustain 4-fold rotational symmetry, wherein A is a trifunctional carboxylate with 3-fold rotational symmetry (allowing for geometric distortion), wherein 'n' indicates a polymeric structure in three dimensions (i.e., $n \geq 2$), and wherein any coordinating ligand or solvent molecule is optionally coordinated to each M.

In each of the above Formulas 1–7, M is a metal preferably in its 2+ transition state. However, it is also contemplated that M can be in other transition states (such as 1+, 3+, and so forth), and structures of the subject invention can contain M in more than one transition state (i.e., M(II)M (III)). For every M that is not in a 2+ transition state, there will preferably exist a counter ion to balance the charge (+ charge if <2; − charge if >2). The anions may, or may not, be coordinated to the metal.

BRIEF DESCRIPTION OF DRAWINGS

The file of this patent contains at least one drawing executed in color. Copies of this patent with color drawings are provided to the Patent and Trademark Office with payment of the necessary fee.

FIG. 4 (left) shows a ball-and-stick model of a square nSBU. FIG. 4 (right) shows the corresponding conformational projection for this molecule.

FIGS. 5A–5D illustrate the linking of molecular squares and FIGS. 5E–5G show space-filling models of the Archimedean faceted nanoball.

FIGS. 6A–6J show various orientations of an isomer configuration of the Archimedean faceted nanoball shown in FIGS. 5A–5G. FIGS. 6A–6G illustrate the linking of molecular squares and FIGS. 6H–6J show space-filling models of the isomer configuration.

FIG. 9 (left) shows a ball-and-stick model of a triangular nSBU. FIG. 9 (right) shows the corresponding conformational projection for this molecule.

FIG. 10A shows a molecular polyhedron of the subject invention with triangular polygons linked at their vertices with a dihedral angle of 70° and 32' (wherein ' equals minutes). FIG. 10B shows a molecular polyhedron with square polygons linked at their vertices with a dihedral angle of 90° dihedral angle. FIG. 10C shows a molecular polyhedron with triangular polygons linked at their vertices with a dihedral angle of 109° and 28'. FIG. 10D shows a molecular polyhedron with square polygons linked to triangular polygons with a dihedral angle of 125° and 16'. FIG. 10E shows a molecular polyhedron with square polygons linked at their vertices with a dihedral angle of 120°. FIG. 10F shows a molecular polyhedron with triangular polygons linked at their vertices with a dihedral angle of 138° and 11'. FIG. 10G shows a molecular polyhedron with molecular pentagons linked at their vertices with a dihedral angle of 160° and 34'. FIG. 10H shows a molecular polyhedron with molecular polyhedrons linked to molecular triangles with a dihedral angle of 142° and 37'. FIG. 10I shows a molecular polyhedron with molecular squares linked at their vertices with a dihedral angle of 144°.

In FIG. 13A, a rhombicuboctahedron (left) and its edge-skeleton (right) are shown. In FIG. 13B, a small cubicuboctahedron (left) and a small rhombihexahedron (right) are shown.

FIG. 20A shows the temperature-dependent molar susceptibility (per nSBU), $\chi$, of the structure of Example 15 at a 0.1 Tesla (data points) overlaid by a plot of the Bleaney-Bowers best fit model (solid line): J=−350 c$^{-1}$ and J'=−18 cm$^{-1}$. FIG. 20B shows the field-dependent magnetization of the structure of Example 15 at T=5 k.

FIG. 21A shows the temperature-dependent molar susceptibility (per nSBU), $\chi$, of the structure of Example 16 at a 0.1 Tesla (data points) overlaid by a plot of the Bleaney-Bowers best fit model (solid line): J=−380 cm$^{-1}$ and J'=−85 cm$^{-1}$. FIG. 21B shows the field-dependent magnetization of the structure of Example 16 at T=5 k.

DETAILED DISCLOSURE OF THE INVENTION

The subject invention pertains to molecular polyhedra constructed of molecular building blocks that approximate polygons (hereinafter molecular polygons), in which the molecular polygons are linked at their vertices. The molecular polygons can comprise metal-organic moieties (also termed nanoscale secondary building units, or nSBUs) or non-metal-organic moieties. The molecular polyhedra of the subject invention can be constructed of molecular polygons (such as triangles, squares, and other polygons), wherein the molecular polygons are linked at their vertices by a linking molecular moiety that subtends the appropriate angle between the planes of the linked molecular polygons.

By virtue of the vertex-linkages between their component polygons, the molecular polyhedra and polymeric structures of the subject invention can have open faces (faceted polyhedra), and can therefore exhibit desirable physical properties, such as porosity. nSBU vertices can be linked via covalent interactions using the coordinating ligands exemplified herein, such as bifunctional or trifunctional carboxylates, as well as other appropriate coordinating ligands. Appropriate coordinating ligands include those angular multifunctional ligands capable of sustaining the desired dihedral angle(s) between nSBUs. Molecular polygons comprising non-metal-organic moieties can be liked at their vertices via non-covalent interactions through bridging ligands. Appropriate bridging ligands include those angular ligands capable of sustaining the desired dehedral angle(s) between non-metal polygons. nSBUs vertices can be liked to vertices of non-metal polygons through bridging ligands, using non-covalent interactions. The appropriate bridging ligands include those angular ligands capable of sustaining the desired dihedral angle(s) between the metal polygon and the non-metal polygon.

The nanoscale polyhedra of the subject invention can exist as discrete macromolecules or be fused, e.g., in order to crystal engineer open framework solids.

Examples of general formulas for polyhedron molecules and polymeric structures of the subject invention that are constructed of metal-organic polygons (nSBUs) include:

Formula 1: $(MA)_{12}$

Formula 1 represents a general formula for molecules of the subject invention having a spheroid architecture (e.g., nanoballs) (90°), wherein M can be any metal that can sustain 4-fold rotational symmetry (such as a molecular square), A is a bifunctional carboxylate ii that subtends an angle of 90° (allowing for geometric distortion), and wherein any coordinating ligand or solvent molecule may optionally be coordinated to each M.

Figure 24A:
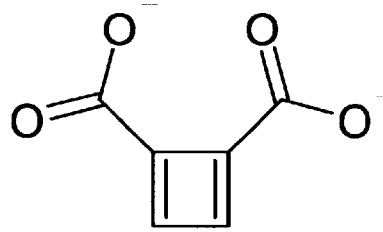
FIGS. 24A–24C show examples of bifunctional carboxylates that subtend an angle of 90°. The angle subtended by the bifunctional carboxylate in FIG. 24B is actually 72°, but can sustain distortion to 90°, as determined by molecular modeling experiments.
Figure 24B:
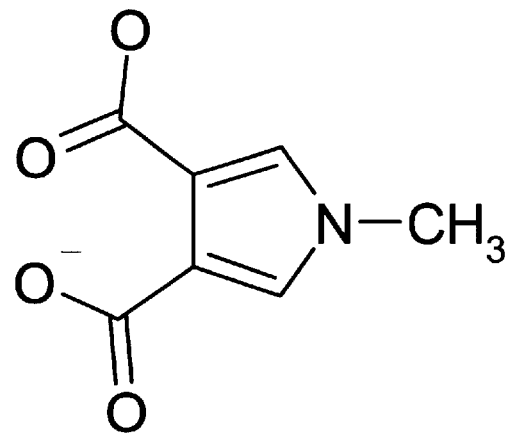
Figure 24C:
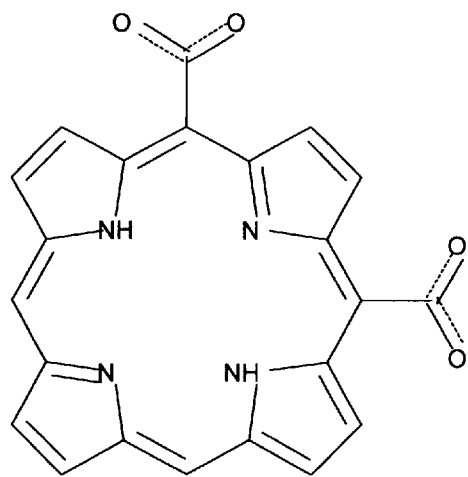

Examples of bifunctional carboxylates that can subtend an angle of 90° are shown in FIGS. 24A–24C. The angle subtended by the bifunctional carboxylate in FIG. 24B is actually 72°, but can sustain distortion to 90°, as determined by molecular modeling experiments.

Formula 2: $(MA)_{24}$

Formula 2 represents a general formula for nanoballs (120°) of the subject invention, wherein M can be any metal that can sustain 4-fold rotational symmetry (such as a molecular square), wherein A is a bifunctional carboxylate that subtends an angle of 120° (allowing for geometric distortion), and wherein any coordinating ligand or solvent molecule may optionally be coordinated to each M.

Formula 3: $(MA)_{60}$

Formula 3 represents a general formula for nanoballs (144°) of the subject invention, wherein M can be any metal that can sustain 4-fold rotational symmetry, wherein A is a bifunctional carboxylate that subtends an angle of 144° (allowing for geometric distortion), and wherein any coordinating ligand or solvent molecule may optionally be coordinated to each M.

Formula 4: $(MA)_n$

Formula 4 represents a general formula for a tetragonal 2D network of the subject invention, wherein M can be any metal that can sustain 4-fold rotational symmetry (such as a molecular square), A is a bifunctional carboxylate that subtends an angle greater than 90°, and preferably subtends an angle of 120°, allowing for geometric distortion, wherein 'n' indicates a polymeric structure, albeit in two dimensions (i.e., $n \geq 4$), and wherein any coordinating ligand or solvent molecule may optionally be coordinated to each M.

Formula 5: $(MA)_n$

Formula 5 represents a general formula for Kagomé 2D network of the subject invention, wherein M can be any metal that can sustain 4-fold rotational symmetry, wherein A is a bifunctional carboxylate that subtends an angle greater than 90°, and preferably subtends an angle of 120°, allowing for geometric distortion, wherein 'n' indicates a polymeric structure, albeit in two dimensions (i.e., $n \geq 3$), and wherein any coordinating ligand or solvent molecule may optionally be coordinated to each M.

Formula 6: $(M^1_4 M^2_3 A_3 Y_2)_n$

Formula 6 represents a general formula for an embodiment of a polymer of the subject invention, as shown in FIGS. 11A–11F, wherein $M^1$ can be any metal that can sustain 3-fold rotational symmetry (such as a molecular triangle), wherein $M^2$ can be any metal that can sustain 4-fold rotational symmetry, wherein A is a trifunctional carboxylate with 3-fold rotational symmetry (allowing for geometric distortion), wherein Y is any –1 anion ("$Y_2$" could also be just one "Y", if Y is a –2 anion), wherein 'n' indicates a polymeric structure in three dimensions (i.e., $n \geq 2$), and wherein any coordinating ligand or solvent molecule is optionally coordinated to each M.

Formula 7: $(M_3 A_2)_n$

Formula 7 represents a general formula for another embodiment of a polymer of the subject invention, as shown in FIGS. 15A–15F, wherein M can be any metal that can sustain 4-fold rotational symmetry (such as a molecular square), wherein A is a trifunctional carboxylate with 3-fold rotational symmetry (allowing for geometric distortion), wherein 'n' indicates a polymeric structure in three dimensions (i.e., $n \geq 2$), and wherein any coordinating ligand or solvent molecule is optionally coordinated to each M.

In each of the above Formulas 2–7, M can be any transition metal and is preferably in its 2+ transition state. It is also contemplated that M can be in other transition states (such as 1+, 3+, and so forth), and structures of the subject invention can contain M in more than one transition state (i.e., M(II)M(III)). For every M that is not in a 2+ transition state, there will preferably exist a counter ion to balance the charge (+ charge if <2; – charge if >2). The anions may, or may not, be coordinated to the metal.

Examples of metals that can sustain 3-fold rotational symmetry include, but are not limited to, metals that sustain tetrahedral, trigonal pyramidal, trigonal bipyramidal, or trigonal planar coordination spheres. Examples of first row transition metals (from the periodic table of the elements) that meet this criterion include Zn(II), Cr(IV), Cr(V), CR(VI), Co(II), Tc(VII), Mn(II), Fe(II), Fe(V), Ni(II), and Cu(II). Preferred metals that can sustain 3-fold rotational symmetry include, for example, Zn(II), Co(II), Ni(II), Fe(II), Cu(II), and Mn(II). Examples of metals that can sustain 4-fold rotational symmetry include, but are not limited to, ions that sustain octahedral, square planar, or square pyramidal coordination spheres. Examples of first row transition metals (from the periodic table of the elements) that meet this criterion g include Ti(III), V(III), Cr(II), Cr(III), Mn(II), Fe(II), Fe(III), Co(II), Ni(II), Cu(II), and Zn(II). Preferred metals that can sustain 4-fold rotational symmetry include, for example, Cr(II), Co(II), Fe(II), Ni(II), Cu(II), and Zn(II).

Bifunctional carboxylates that can subtend an angle of 90° include, but are not limited to, those shown in FIGS. 24A–24C.

Figure 2A:
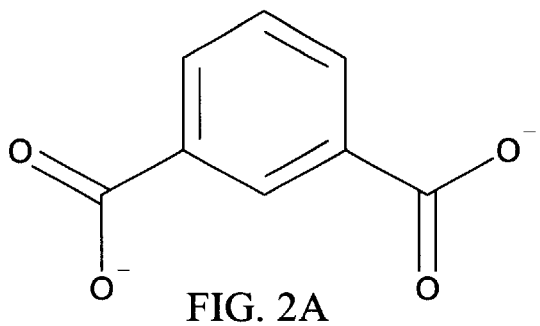
FIGS. 2A–2NN illustrate representative ligands for 120°.
Figure 2B:
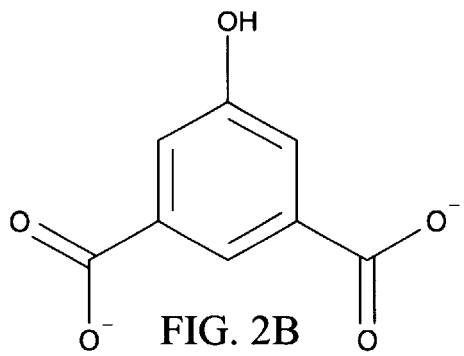
Figure 2C:
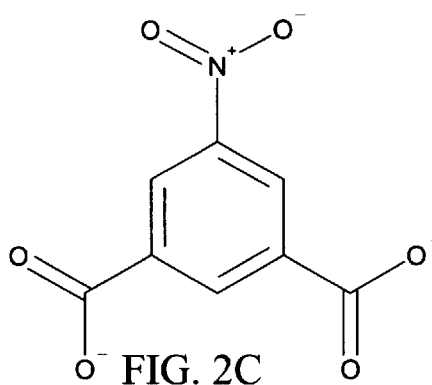
Figure 2D:
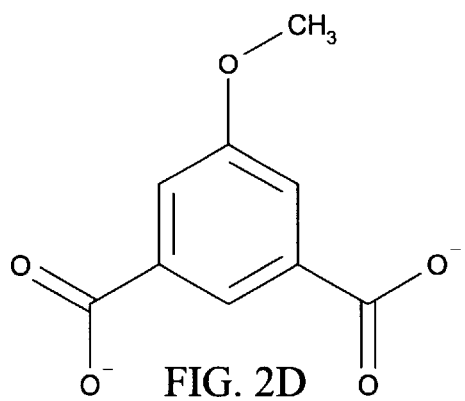
Figure 2E:
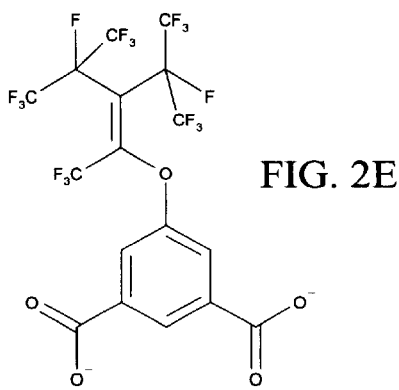
Figure 2F:
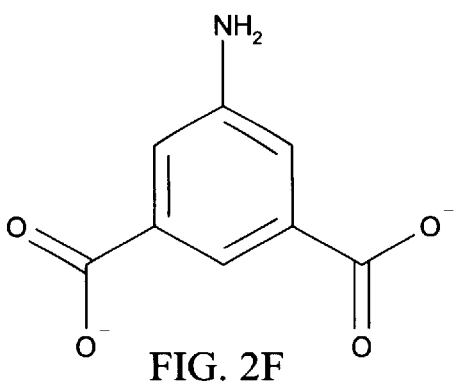
Figure 2G:
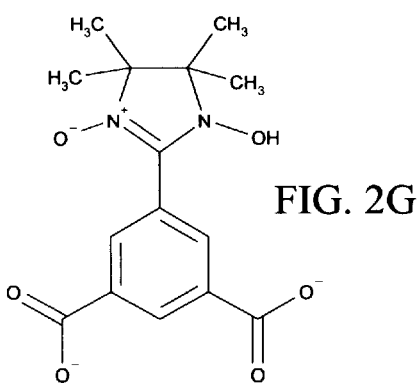
Figure 2H:
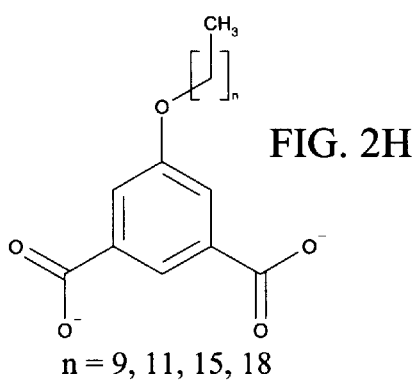
Figure 2I:
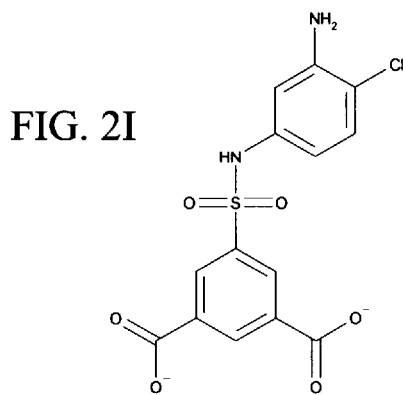
Figure 2J:
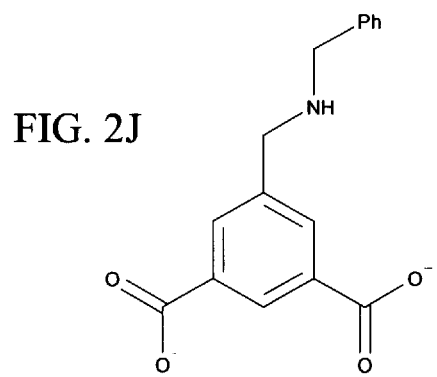
Figure 2K:
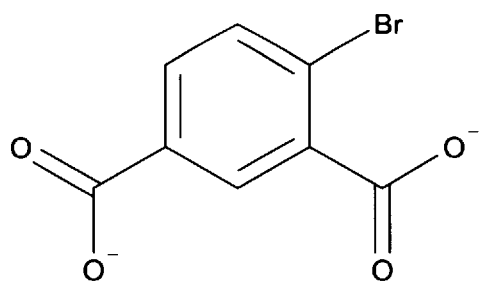
Figure 2L:
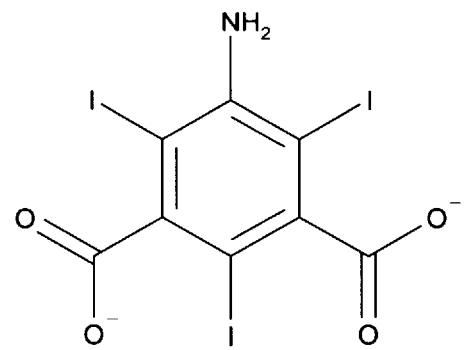
Figure 2M:
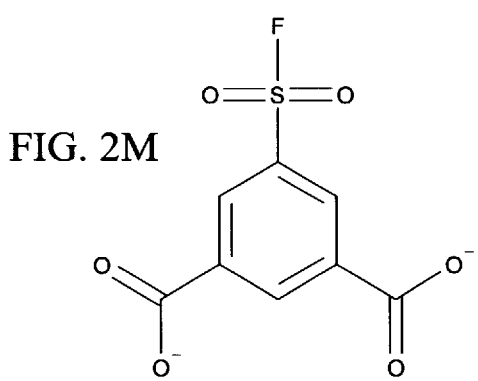
Figure 2N:
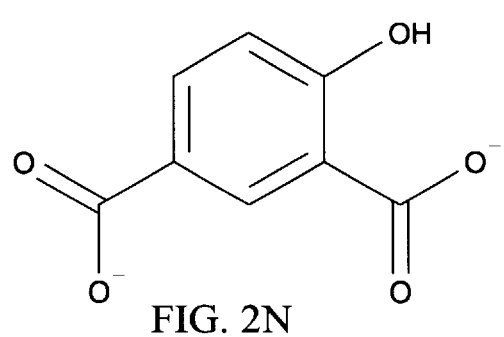
Figure 2O:
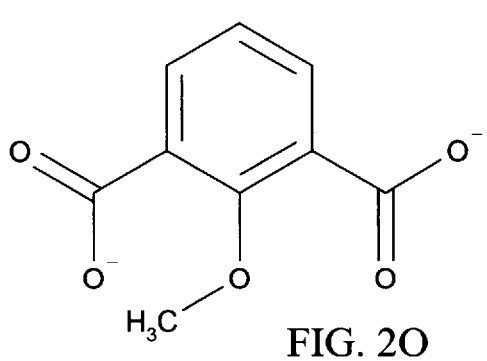
Figure 2P:
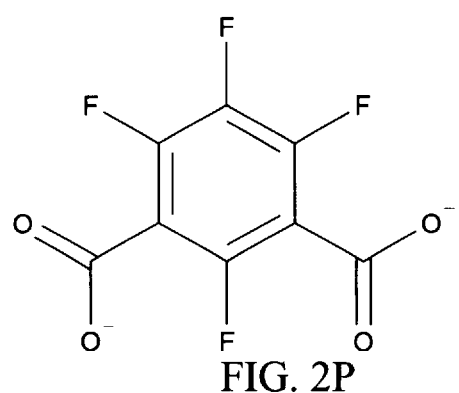
Figure 2Q:
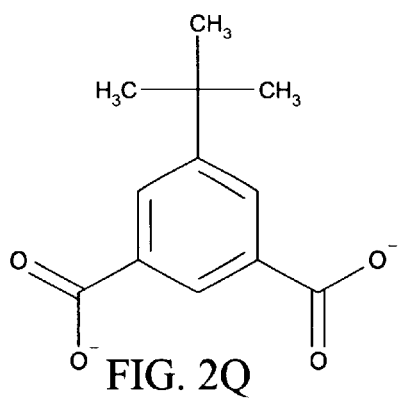
Figure 2R:
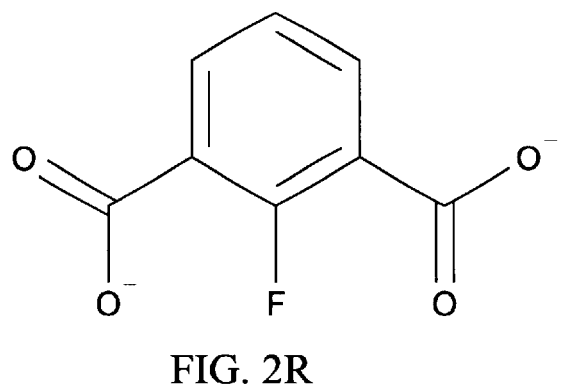
Figure 2S:
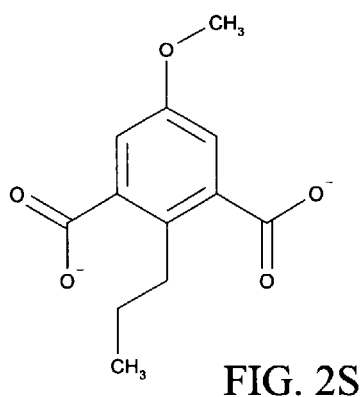
Figure 2W:
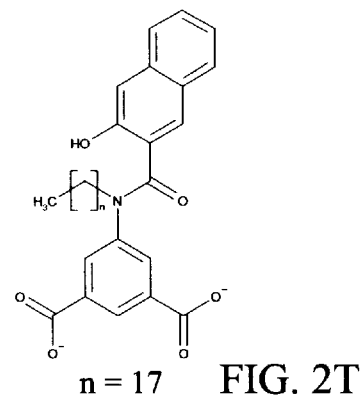
Figure 2U:
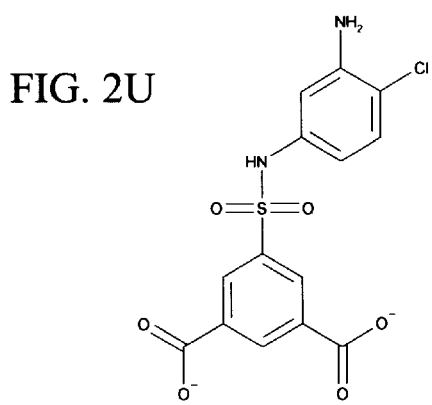
Figure 2V:
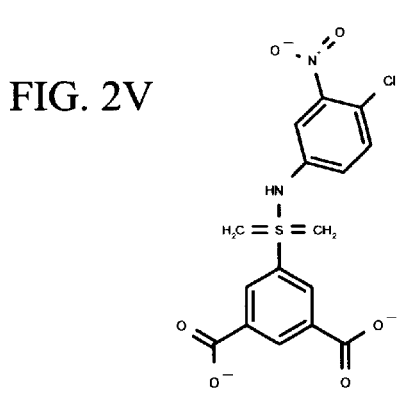
Figure 2W:
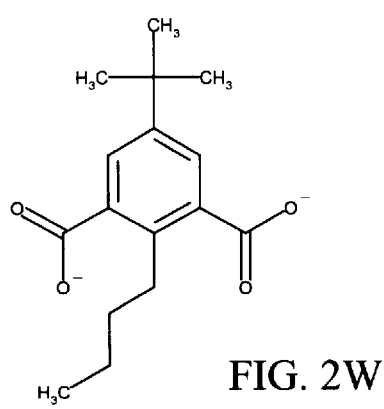
Figure 2X:
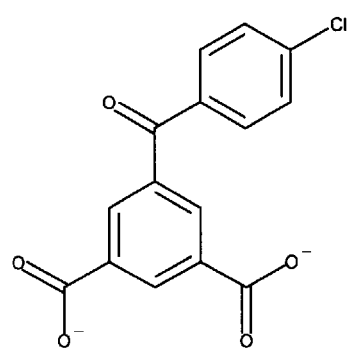
Figure 2Y:
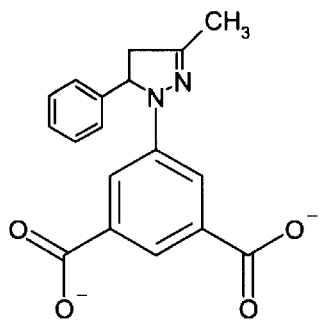
Figure 2Z:
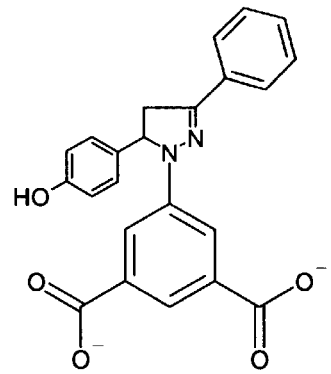
Figure 2A:
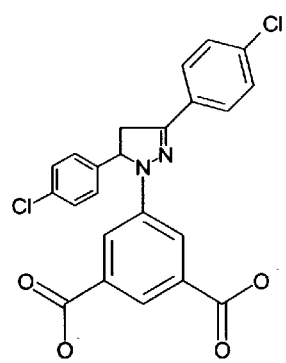
Figure 2B:
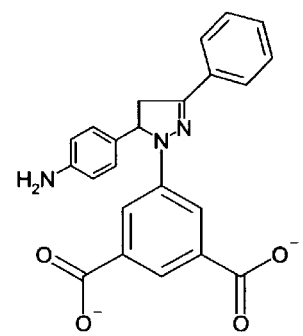
Figure 2:
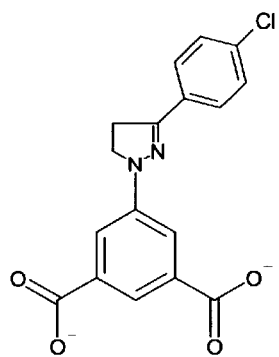
Figure 2:
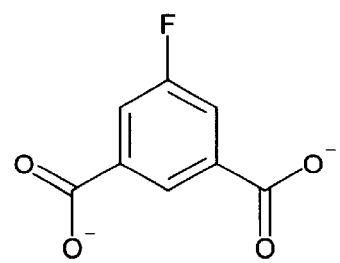
Figure 2:
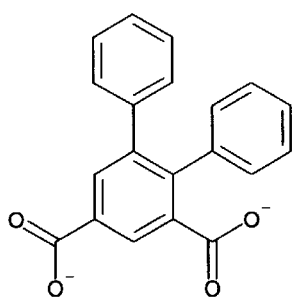
Figure 2:
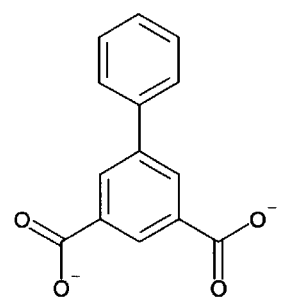
Figure 2:
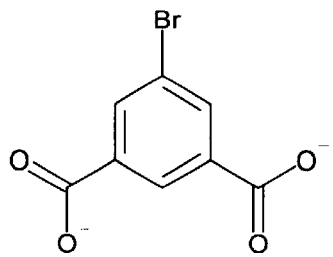
Figure 2:
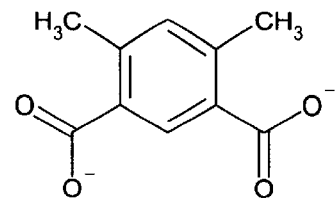
Figure 2:
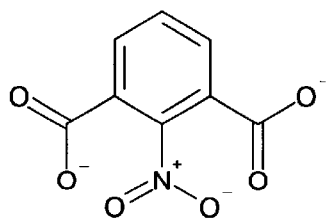
Figure 2:
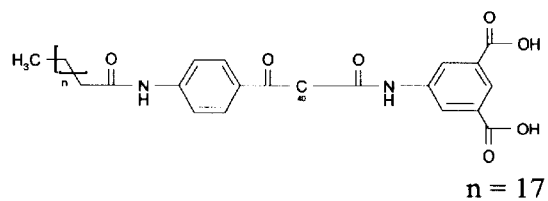
Figure 2:
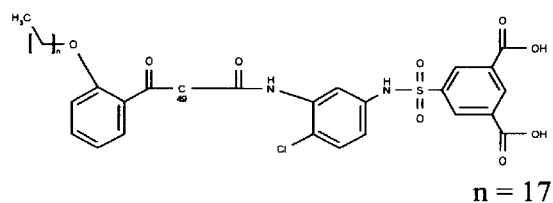
Figure 2:
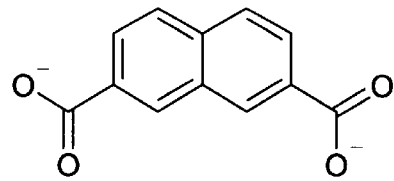
Figure 2:
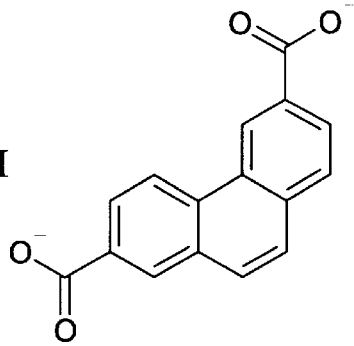
Figure 2:
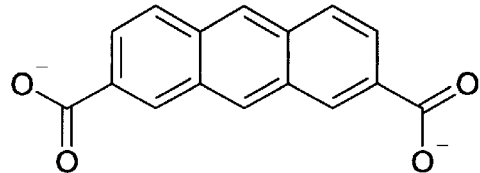

Bifunctional carboxylates that can subtend an angle of 120° include, but are not limited to, those shown in FIGS. 2A–2NN. Preferred bifunctional carboxylates that can subtend an angle of 120° include 1,3-benzenedicarboxylate, 5-hydroxy-1,3-benzenedicarboxylate, 5-nitro-1,3-benzenedicarboxylate, and 5-alkyl-1,3-benzenedicarboxylates.

Bifunctional carboxylates that can subtend an angle of 144° include, but are not limited to, those shown in FIGS. 3A–3G. Preferred bifunctional carboxylates that can subtend an angle of 144° include 2,4-pyrroledicarboxylate, N-methyl-2,4-pyrroledicarboxylate, 2,4-furandicarboxylate and 1,3-cyclopentadiendicarboxylate.

Trifunctional carboxylates that can sustain 3-fold rotational symmetry include, but are not limited to 2-, 4- and/or 6-substituted 1,3,5-benzenetricarboxylates. Preferred trifunctional carboxylates that can sustain 3-fold rotational symmetry include 1,3,5-benzenetricarboxylate.

Figure 10A:
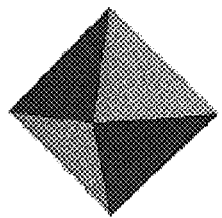
FIGS. 10A–10I show a schematic with illustrations of nine faceted polyhedra of the instant invention.
Figure 10B:
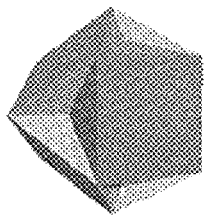
Figure 10C:
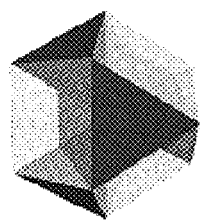
Figure 10D:
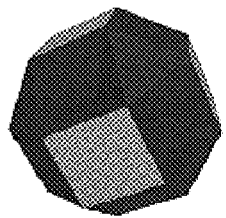
Figure 10E:
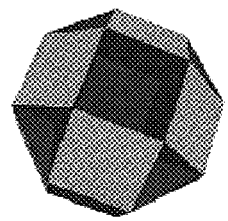
Figure 10F:
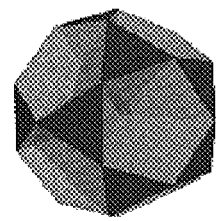
Figure 10G:
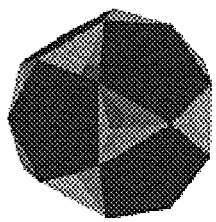
Figure 10H:
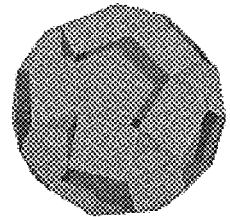
Figure 10I:
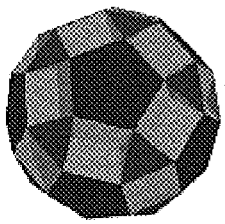
Figure 11A:
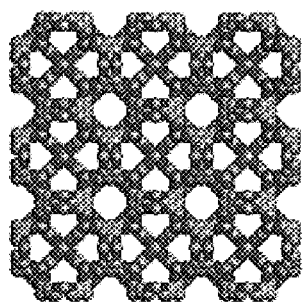
FIGS. 11A–11C and 11D–11F show two further examples, respectively, of networks derived from the crystal structures of the instant invention.
Figure 11B:
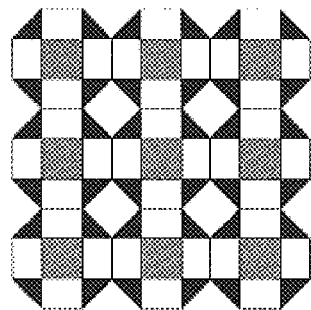
Figure 11C:
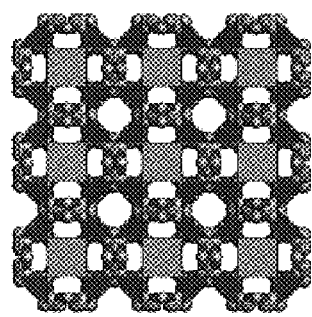
Figure 11D:
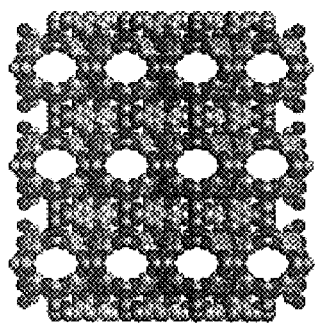
Figure 11E:
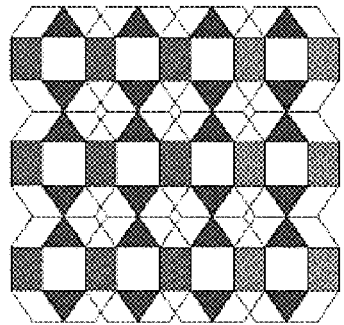
Figure 11F:
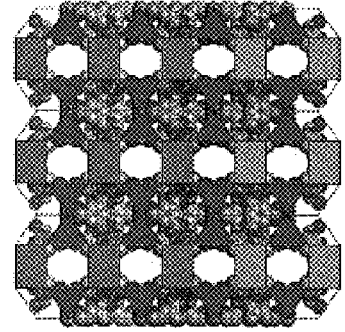

Additional examples of general formulas for polyhedron molecules of the subject invention that are constructed of metal-organic polygons (nSBUs) include: Formula 8: $(M_4 A_3)_2$, which is a tetrahemihexahedron, shown in FIG. 10A; Formula 9: $(M_4 A_3)_4$, which is a octahemioctahedron, shown in FIG. 10C; Formula 10: $(M_7 A_6)_4$, which is a small cubicuboctahedron, shown in FIG. 10D; Formula 11: $(M_4 A_3)_{10}$, which is a small icosihemidodecahedron, shown in FIG. 10F; and Formula 12: $(M^1_6 A^1_5)_4$, which is a small dodecicosidodecahedron, shown in FIG. 10H.

Examples of general formulas for polyhedron molecules of the subject invention that are constructed of non-metal-organic polygons include: Formula 13 (a small rhombidodecahedron): $S_{12}B_{24}$, wherein S is a non-metal molecular square, such as that shown in FIG. 27, and B is a bridging ligand, such as that shown in FIG. 29; and Formula 14 (small cubicuboctahedron): $S_6 T_8 B_{24}$, wherein S is a non-metal molecular square, such as that shown in FIG. 27, T is a non-metal molecular triangle, such as that shown in FIG. 28, and B is a bridging ligand, such as that shown in FIG. 28.

The molecular building blocks of the present invention are preferably, but not limited to, those containing metal-organic moieties (nSBUs). Advantages inherent in the utilization of nSBUs include: (i) metal-organic coordination polymers can be prepared via self-assembly, allowing inexpensive synthesis, often with one step and high yield (e.g., "one pot" reactions); structures having metal-organic nSBUs are inherently modular since they contain at least two components, a node (e.g., the nSBt) and a "spacer" (e.g., a multifunctional organic coordinating ligand); structures having nSBUs can have an open framework, which conveys the ability to gain very precise control over cavities and channels; metal organic coordination polymers are typically of low solubility and, therefore, kinetic and thermodynamic products can be formed for a particular set of components, making them useful for sorption from, and to, solution phases; and metal-organic incorporating structures tend to be moderately thermally stable and air and water stable (many compounds of the subject invention are stable to 200° C. and others are stable at or above 400° C.). In addition, the use of nSBUs are particularly useful for the construction of molecular polyhedra (and compounds comprising such molecular polyhedra) that can exhibit one or more advantageous properties, such as magnetic activity, luminescent activity, phosphorescent activity, fluorescent activity, and catalytic and redox activity.

Figure 27:
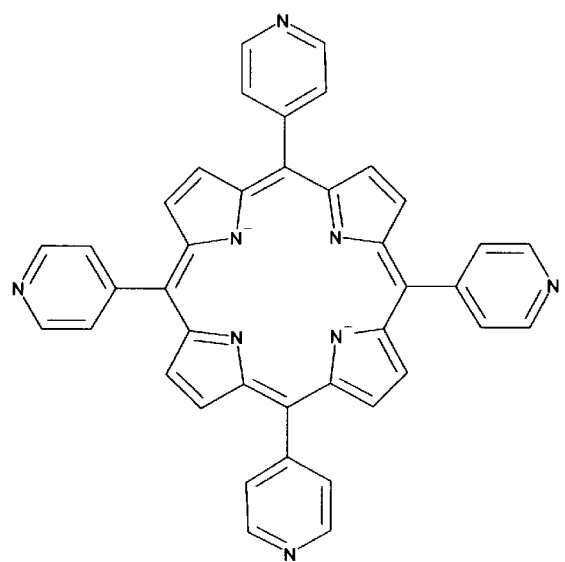
FIG. 27 shows an example of a molecular polygon that does not comprise a metal-organic moiety. The molecular polygon shown is a non-metal molecular square.
Figure 28:
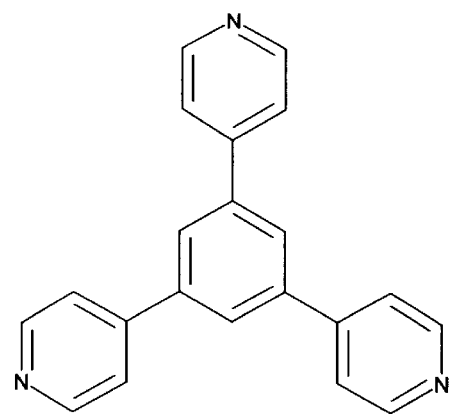
FIG. 28 shows another example of a molecular polygon that does not comprise a metal-organic moiety. The molecular polygon shown is a non-metal molecular triangle.
Figure 29:
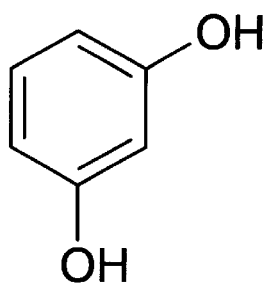
FIG. 29 shows an example of a bridging ligand (1,3-dihydroxybenzene) that subtends an angle of about 120°. The bridging ligand shown can be utilized, for example, to link the non-metal molecular polygons shown in FIGS. 27 and 28.

The subject invention also concerns molecular polyhedron molecules that are constructed of building blocks that are not based upon metal-organic moieties. Polyhedron-shaped molecules of the subject invention can be constructed from any molecular, or supramolecular, moieties that approximate molecular polygons, and which can be connected by a linking molecular moiety that subtends the appropriate angle. Examples of molecular building blocks that do not comprise metal-organic moieties are shown in FIG. 27 (non-metal molecular square) and FIG. 28 (non-metal molecular triangle). FIG. 29 shows an example of a bridging ligand that is appropriate to connect the vertices of non-metal molecular polygons, such as those shown in FIGS. 27 and 28, and which subtends an angle of about 120°.

Edge-sharing of molecular polygons affords closed convex polyhedra, such as tetrahedrons or octahedrons, whereas connection of vertices generates open structures that are edge-skeletons of such polyhedra. Platonic and Archimedean solids are part of a larger classification of polyhedra called uniform polyhedra. There is a subset of nine uniform polyhedra that have congruent edge-skeletons with the Platonic and Archimedean solids, but differ only in that they have both concave and convex faces, as shown in FIGS. 10A–10I. Of particular relevance to the subject invention are the convex faces of these nine polyhedra, which are a set of polygons connected at their vertices and have both open and closed faces. The resulting nine closed sets of polygons that are sustained by vertex-linked triangles, squares, pentagons, or combinations thereof, are termed "faceted uniform polyhedra."

Figure 1A:
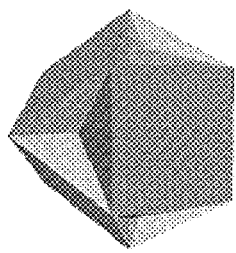
FIGS. 1A–1C show cubohemioctahedron, small rhombihexahedron and small rhombidodecahedron uniform polyhedra, respectively, formed by linking vertices of squares only.
Figure 1B:
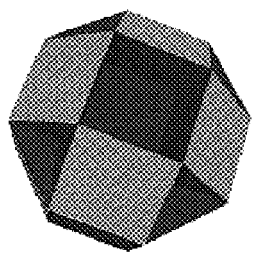
Figure 1C:
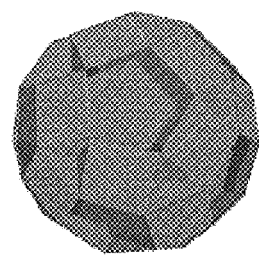

As shown in FIG. 1, there are at least three faceted uniform polyhedra that can be generated by linking the vertices of only squares. From a design and control perspective, the most important consideration about faceted polyhedra is the dihedral angle between the planes of the polygons that are linked at their vertices. In the case of the three faceted uniform polyhedra that can be built from squares only, which one occurs will be strongly influenced by the angle subtended by the "spacer" moiety that links the vertices, e.g.: cubohemioctahedron (90°), small rhombihexahedron (120°), and small rhombidodecahedron (144°). Therefore, judicious control of the angle subtended by the vertices of the squares affords control over which polyhedron will result. Representative ligands for each angle include, but are not limited to, those ligands shown in FIGS. 2A–2NN for 120° and FIGS. 3A–3G for 144°.

Figure 4:
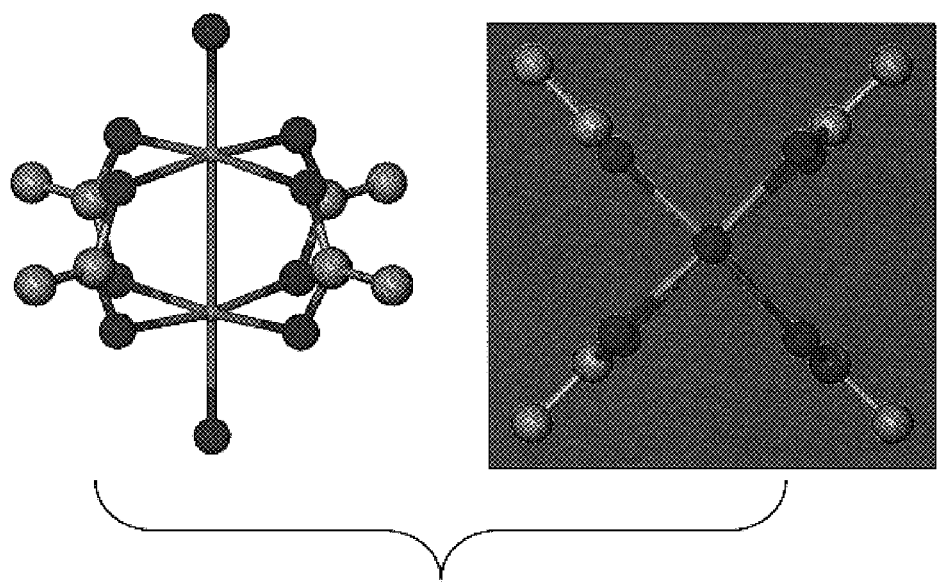
FIG. 4 shows the square nanoscale secondary building unit (nSBU), described by the general formula, $M_2(RCO_2)_4$, such as $[Cu_2(PhCOO)_4]$.
Figure 5A:
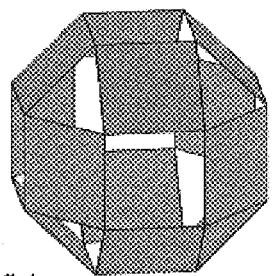
FIGS. 5A–5G show various orientations of an Archimedean faceted nanoball configuration.
Figure 5B:
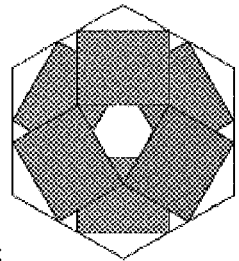
Figure 5C:
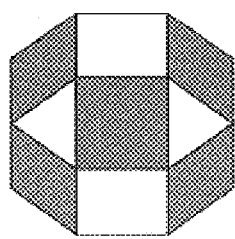
Figure 5D:
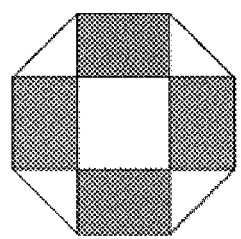
Figure 5E:
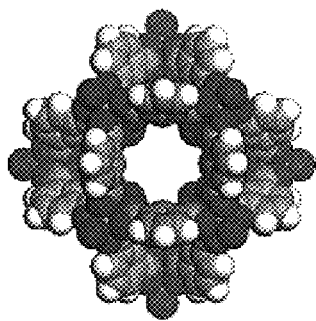
Figure 5F:
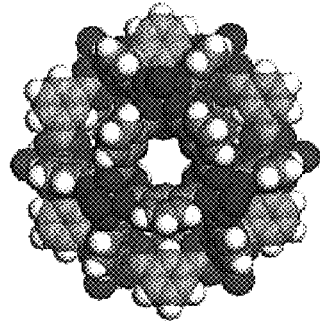
Figure 5G:
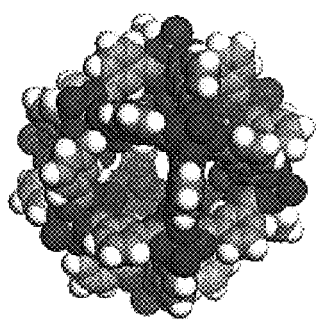

FIG. 4 shows a molecularly square-shaped nanoscale secondary building unit (nSBU). Square nSBUs can be described by the general formula: $M_2(RCO_2)_4$, where M is selected from a group that includes any transition metal, Group I metal, Group II metal, Group III metal, Group IV metal, lanthanide or actinide metals; and R is selected from any moiety that contains an additional carboxylate unit.

The molecule shown in FIG. 4 has heretofore been known and is present in the Cambridge Structural Database. However, in the instant invention, the use of benzene-1,3-dicarboxylate (bdc) and 1,3,5-benzene tricarboxylate (btc) complexed with CU(II) produced novel infinite and discrete architectures.

The molecular polygons that can be used to construct the molecular polyhedra and polymeric structures of the subject invention include, for example, molecular squares, molecular triangles, molecular pentagons, molecular octagons, molecular hexagons, and molecular n-gons. For example, squares, triangles, and pentagons can be utilized to construct molecular polyhedra of the subject invention. Octagons, hexagons, and n-gons can be utilized to construct the 2-dimensional structures of the subject invention.

The molecular polyhedra of the subject invention can be used in a great variety of industrial applications. For example, the molecular polyhedra of the subject invention can contain active chromophores in either, or both, the molecular building block and the linking moiety. For example, a coordinating ligand can be selected for chemiluminescence as well as its structural features, and a metal can be selected for its magnetic properties. Further uses for the molecular polyhedra of the subject invention can readily be found in the area of catalysis. Moieties known to be catalytically active in solution can be incorporated into the molecular polyhedra structures. For example, square planar metal moieties can be readily incorporated into $\{[XL_2Zn_2(btc)_1]_8[L_2Zn_2(btc)_{1.333}]_3\}_n$ or $\{[Zn_2(btc)_{1.33}]\}_n$. Rhodium and cadmium are metals also known to be catalytically active.

References to molecular polygons of various shapes (e.g., triangle, square) are made throughout the subject specification. It will be understood by those of ordinary skill in the art that these shapes describe the approximate geometric structure of molecules in space (e.g., conformation), which is based on the arrangement of bonds on each molecule's constituent atoms. Angles of coordinating ligands are likewise based upon conformation. Conformational analysis of molecules can be carried out by those of ordinary skill in the art, using routine techniques.

The polyhedra and polymeric structures of the instant invention (and compositions comprising them) are useful in numerous applications because of their novel and desirable structures, and properties. For example, their inherent porosity can be exploited in gas storage, separations, chemosensors, biosensors, remediation of environmental pollutants, drug delivery, and other applications. The polyhedra of the subject invention can contain catalytic sites for use in homogeneous and heterogeneous catalytic processes. The polyhedra of the subject invention can exhibit high thermal motion, which makes them useful for liquid crystalline, lubricants, and thermoelectric materials. The polyhedra of the subject invention can exhibit magnetic properties, which make them useful for information storage or sensing. The polyhedra of the subject invention can have the ability to bind to biomolecules, making them useful in the formation of biomaterials, or for therapeutic applications. Polyhedra of the subject invention having excited state photochemistry make them useful as fluorescent or luminescent probes. The solubility of the polyhedra of the subject invention makes them useful as additives to polymers. In addition, their redox properties make the polyhedra of the subject invention useful for applications which require electron storage and/or transfer.

The terms "building blocks", "polygon moieties", and "molecular polygons" and "polygons" are used herein interchangeably to refer to those polygon-shaped moieties which contribute to the polyhedron-shaped structure of the polyhedron molecules and polymeric structures of the subject invention. More specifically, these terms are used herein to refer to a molecule that has external chemical functionalities which are arranged such that the functionalities can be considered to lie at the vertices of a polygon.

The terms "metal polygon", "metal-organic polygon, "metal building block", metal-organic building block", "small or secondary building units", "SBU", "nanoscale SBU", and "nSBU" are used herein interchangeably to refer to those building blocks comprising a metal-organic moiety.

The term "non-metal-organic polygon" and "non-metal polygon" are used herein interchangeably to refer to those building blocks which lack a metal-organic moiety.

The terms "linking moiety", "linker", and "spacer" are used herein interchangeably to refer to those moieties which connect vertices of two or more building blocks of the molecular polyhedra of the subject invention, and are intended to be inclusive of the terms "coordinating ligand" and "bridging ligand".

The term "coordinating ligand" is used herein to refer to those moieties which connect vertices of two or more metal-organic polygons, such as through covalent interactions.

The term "bridging ligand" is intended to refer to those moieties which connect vertices of two or more non-metal-organic polygons, or which connect the vertices of a metal-organic polygon and a non-metal-organic polygon, such as through non-covalent interactions.

The term "0D" is used herein in its crystal engineering sense to refer to a structure that has finite dimensions in all three dimensions (also known as a discrete structure).

The term "1D" is used herein in its crystal engineering sense to refer to a structure that can be infinite in one dimension and has finite dimensions in two dimensions, such as a string.

The term "2D" is used herein in its crystal engineering sense to refer to a structure that can be infinite in two dimensions, and finite in one dimension.

The term "3D" is used herein in its crystal engineering sense to refer to a structure that can be infinite in all three dimensions.

All patents, patent applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Synthesis of a Discrete Square SBU with Pyridine as Apical Ligand

Procedure: 0.232 g $Cu(NO_3)_2.2.5H_2O$ (1 mnmol) was dissolved in 4 ml of methanol. An additional solution of 0.244 g (2 mmol) of benzoic acid was dissolved in 4 ml of methanol along with 0.24 ml of pyridine (3 mmol). Both solutions were mixed together very slowly and left to sit under ambient conditions to allow for slow evaporation. After a day or two greenish-blue crystals were formed from the solution.

Analysis: Crystallography: a=10.134, b=10.53, c=17.46, β=98.45, space group: $P2_1/n$, Volm=1842.94.

IR Spectrum: intense peak at 1395 $cm^{-1}$.

Solubility: soluble in dichloromethane, pyridine, and toluene/pyridine mixture.

Here, a molecule based on self-assembly of molecular squares formed a small rhombihexahedron by layering of methanolic $Cu(NO_3)_2.2.5H_2O$ and $H_2bdc$ onto a solution of pyridine that contains templates such as nitrobenzene or 1,2-dichlorobenzene.

EXAMPLE 2

Synthesis of a Spherical Discrete Crystal

Procedure: 0.232 g $Cu(NO_3)_2.2.5H_2O$ (1 mmol) was dissolved in 4 ml of methanol and 3 ml of nitrobenzene. A second solution of 0.166 g (1 mmol) of 1,3-bdc was dissolved in 4 ml of methanol and 0.24 ml of pyridine (3 mmol). After slow diffusion of the 1,3-bdc solution over the $Cu(NO_3)_2.2.5H_2O$ solution, greenish-blue crystals were formed within hours.

Analysis: Crystallography: a=26.17, b=27.7607, c=28.4356, α=92.719, β=96.395, γ=92.681, space group: P-1, Volm=20478.5.

TGA: around 40% weight loss before decomposition at around 250° C.

IR Spectrum: three intense peaks at 1380 $cm^{-1}$, 1345 $cm^{-1}$, and 1520 $cm^{-1}$, XPD: broad XPD pattern has been observed Solubility: sparingly soluble in common organic solvents but slightly soluble in boiling nitrobenzene.

Figure 16:
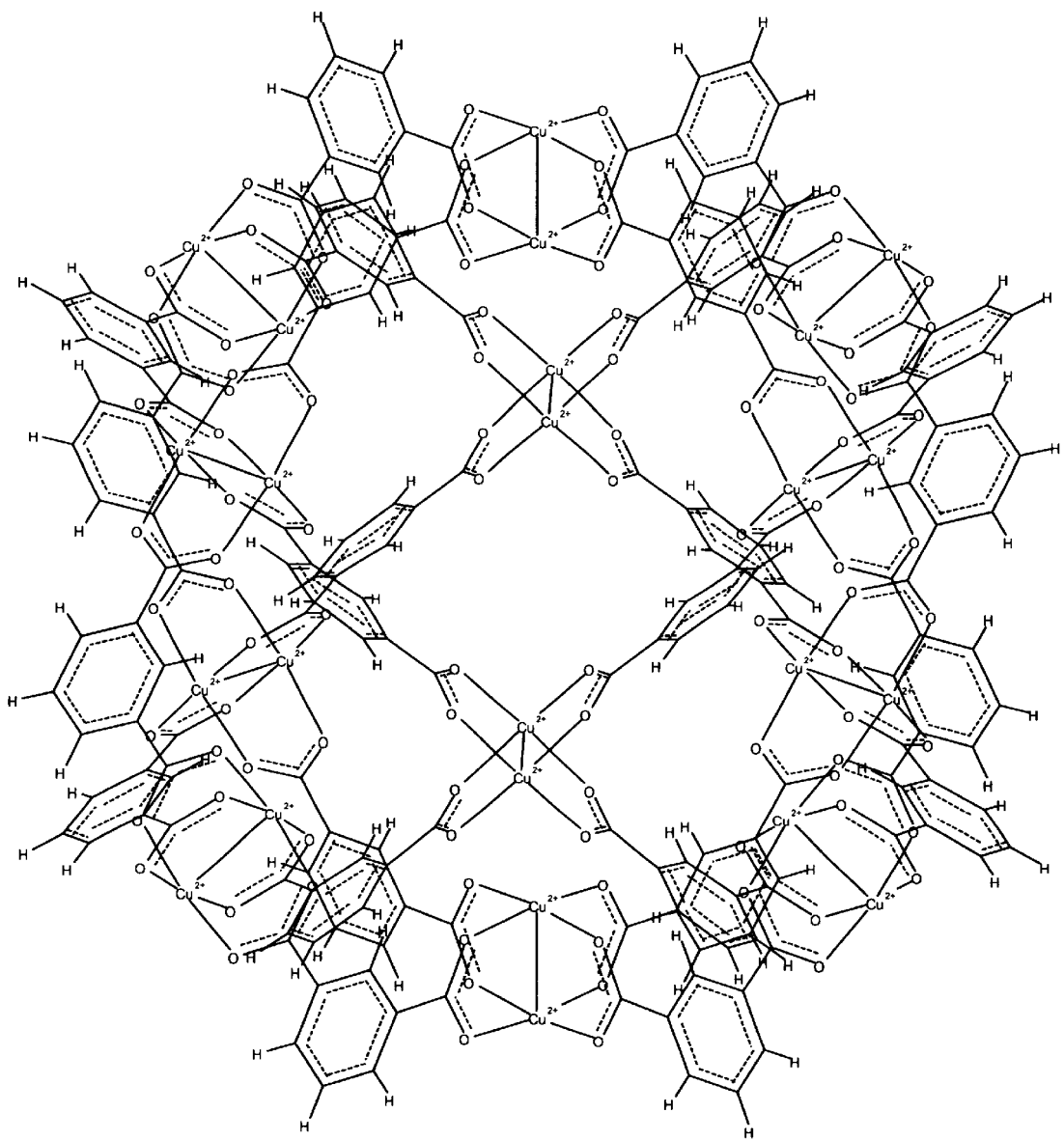
FIG. 16 shows the chemical bonds of a sphere according to the subject invention.
Figure 17:
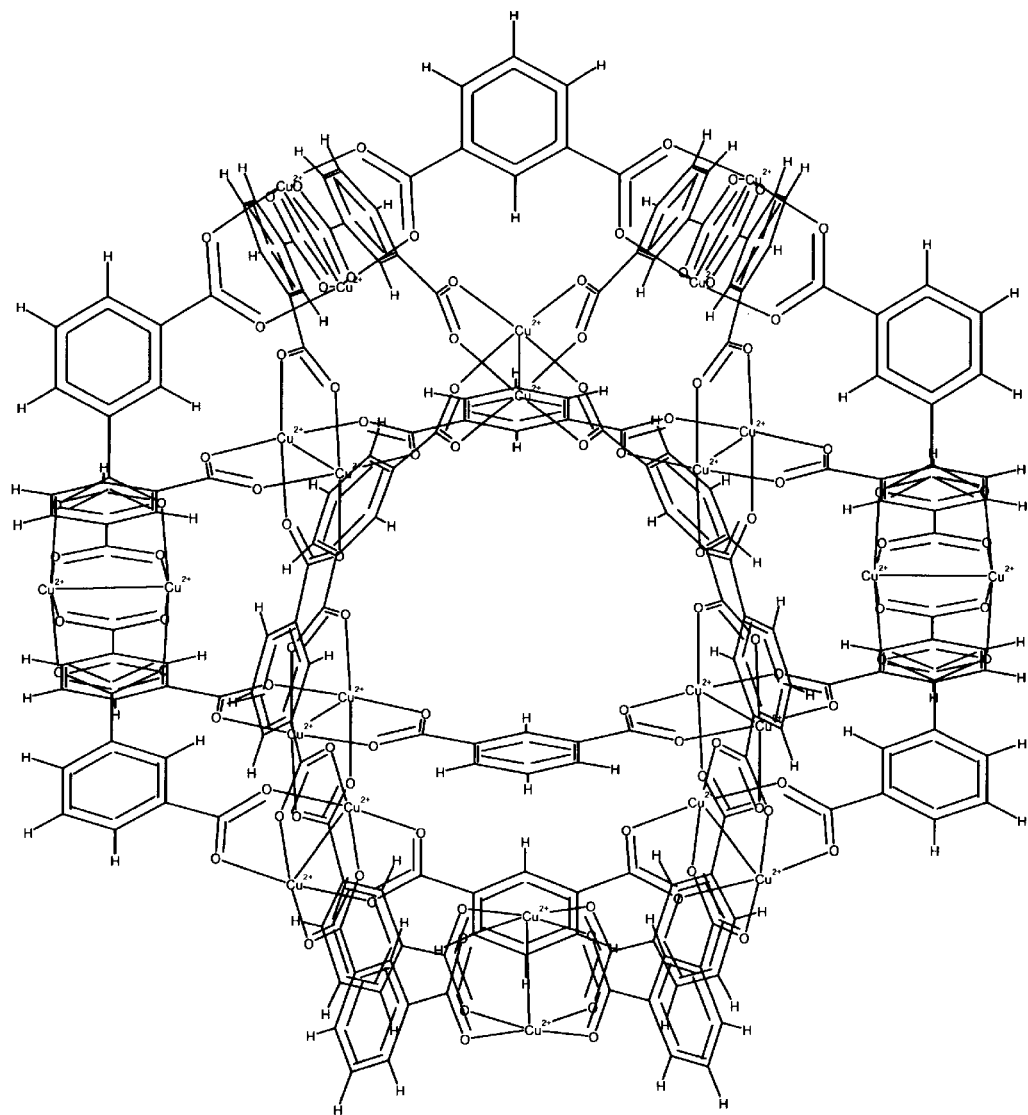
FIG. 17 shows a distorted version of the molecule of FIGS. 6A–6J.
Figure 18A:
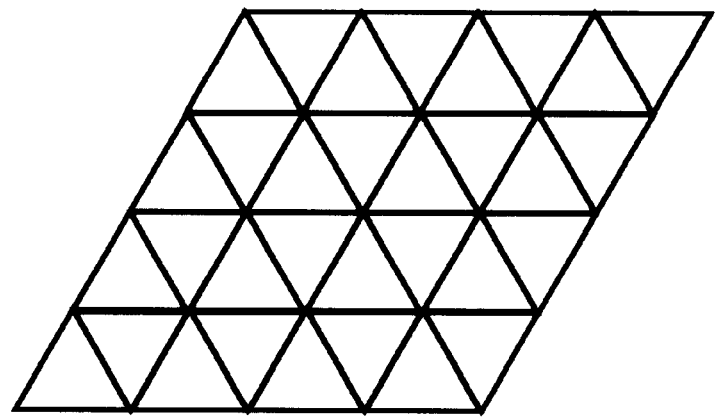
FIGS. 18A and 18B are a schematic representation of triangular and Kagome lattices, respectively.
Figure 18B:
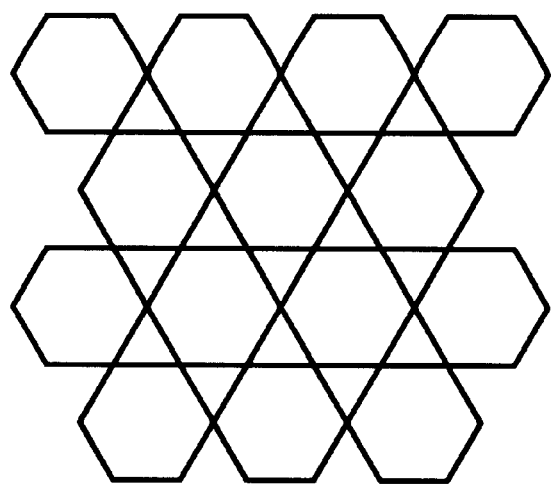
Figure 19A:
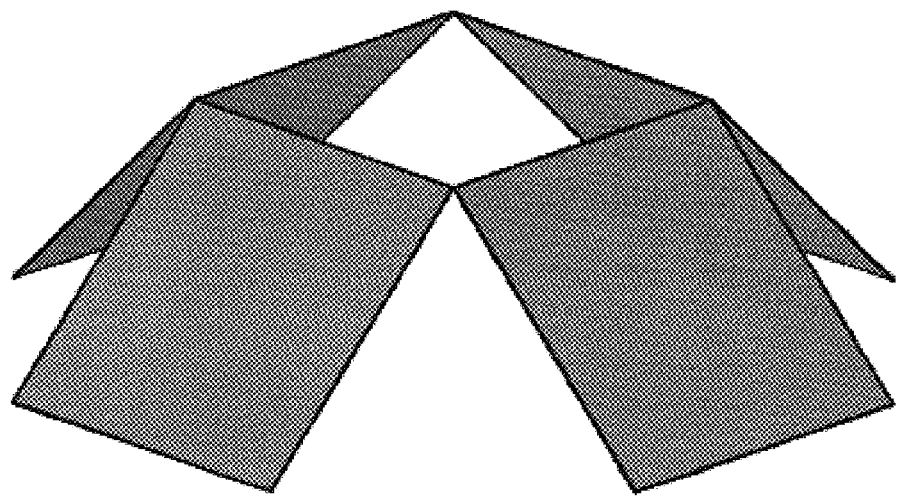
FIGS. 19A and 19B are other representations of square and triangular nSBUs, respectively, that can be formed by linking the vertices of molecular squares.
Figure 19B:
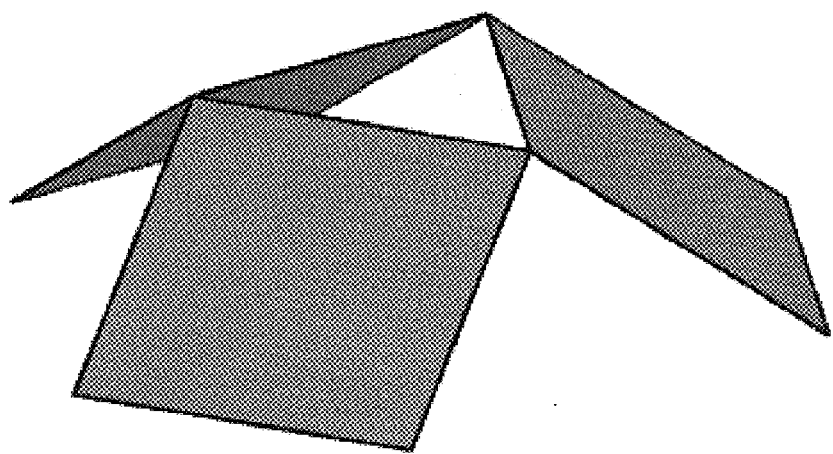

The single crystals of $[(L)(S)Cu_2(bdc)_2]_{12}$, where L=pyridine and S=methanol, which formed as shown in FIGS. 5A–5G revealed a structure composed of vertex-linked molecular squares that had self-assembled into small rhombihexahedra. The schematic shown in FIGS. 5A–5D illustrates how the linking of molecular squares generates the edge-skeleton structure. This molecule contained pyridine ligands at the interior surface that were bonded to the metal ions located at the exterior surface and MeOH ligands at the interior surface metal binding sites. A schematic of this structure is shown in FIG. 16.

It was also observed that the large bowl-shaped square and triangular voids or windows provided access to the interior of the molecule. Disordered solvent was found in these voids or windows and in the 1-$nm^3$ internal cavity, which was determined to be large enough to encapsulate $C_{60}$. There was high thermal motion and disorder in the ligands and the guest molecules, but the structure of the core was determined to be well-defined and unambiguous. The molecular volume was determined to be greater than 10 $nm^3$, and the molecular weight was 6.80 kDa.

Another embodiment is shown in FIGS. 6A–6J. In this instance, an isomer of the small rhombihexahedron described before is crystallized under similar conditions except that 2,6-dimethylpyridine, a non-coordinating base, is used instead of pyridine. The crystal structure formed is represented by $[(S)_2Cu_2(bdc)_2]_{12}$, where S=methanol. Here, the composition differs in the nature of the apically coordinated ligands on the SBU and the connectivity of the SBU. For ease of comparison, FIGS. 22A–22D show various orientations of an Archimedean faceted nanoball configuration, and FIGS. 23A–23G show various orientations of the isomer configuration of the Archimedean faceted nanoball.

Figure 22:
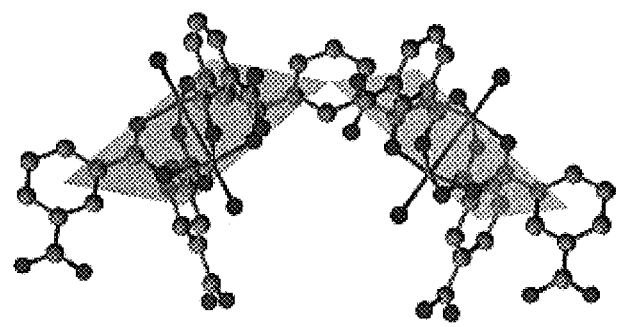
FIG. 22 shows an example of the conformation of a benzene-1,3-dicarboxylate (bdc) ligand that produces the 0D (discrete) nanoballs of the subject invention.

An example of the conformation of a bdc ligand that produces the 0D nanoballs of the subject invention is shown in FIG. 22.

EXAMPLE 3

Synthesis of a Second Discrete Crystal

Procedure: 0.2326 g $Cu(NO_3)_2.2.5H_2O$ (1 mmol) was dissolved in 5 ml of methanol and 3 ml of nitrobenzene. A second solution of 0.166 g (1 mmol) of 1,3-bdc dissolved in 5 ml of methanol, and 0.24 ml of 2,6-dimethylpyridine (3 mmol) was also prepared. After slow diffusion of the 1,3-bdc solution over the $Cu(NO_3)_2.2.5H_2O$ solution, greenish-blue crystals formed after a day.

EXAMPLE 4

Synthesis of a Third Discrete Crystal

Procedure: 0.2326 g $Cu(NO_3)_2.2.5H_2O$ (1 mmol) was dissolved in 5 ml of methanol and 3–4 ml of 1,2-dichlorobenzene. A second solution of 0.166 g (1 mmol) of 1,3-bdc dissolved in 5 ml of methanol, and 0.24 ml of 2,6-dimethylpyridine (3 mmol) was also made. Slow diffusion of the second solution over the first solution again yielded green crystals.

Analysis of Examples 3 and 4: Crystallography: a=28.2539, b=28.2539, c=28.5533, $\gamma$=120, space group: $P6_3/m$, Volm=19739.84.

TGA: around 38% weight loss before decomposition at around 250° C.

IR Spectrum: three intense peaks at 1380 $cm^{-1}$, 1341 $cm^{-1}$, and 1518 $cm^{-1}$ XPD: broad XPD pattern observed Solubility: sparingly soluble in common organic solvents, except for isopropanol, ethyl acetate, DMSO, and DMF; and slightly soluble in nitrobenzene.

In this instance, the molecular weight was 6.23 kDa, and the molecular volume was approximately 10 $nm^3$.

The structure formed by Example 2 exhibited body-centered cubic packing, and the structure of Examples 3 and 4 was hexagonal close packing. Molecular modeling indicated insignificant difference in terms of torsional strain between the two structures.

Other features of the instant crystals were: (a) they are neutral and soluble in organic solvents; (b) they are chemically robust because of the stability of the square SBU; (c) they are likely to be chemically diverse because of the ability to be made from a wide variety of metals, including magnetically active and catalytically active metals; and (d) they both have internal and external sites that are suitable for much larger structures by acting as the node of infinite networks or as the core of mesoscale dendritic structures, since their interior cavities can be accessed via triangular or square voids or windows, and they are bowl-shaped, which means they can contain organic or other chemical species as their guests. The thermal stabilities are consistent with their structures and molecular components. In addition, the crystals appear stable indefinitely when in contact with their mother liquor. When heated, weight losses of 36.9 and 38.3%, respectively, were observed, and this was consistent with corresponding loss of guest molecules. The samples do not remain as single crystals when heated. Loss of coordinated molecules occurs at higher temperatures.

Figure 7A:
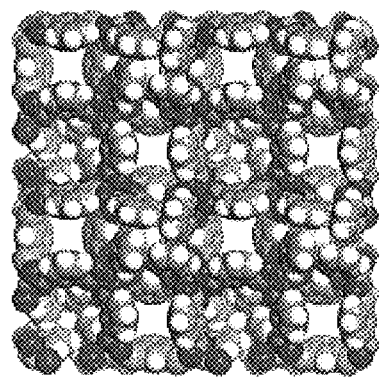
FIGS. 7A–7C show space-filling and schematic representations of the arrangement of square nSBUs in the nanoscale square lattice structure described in Example 16.
Figure 7B:
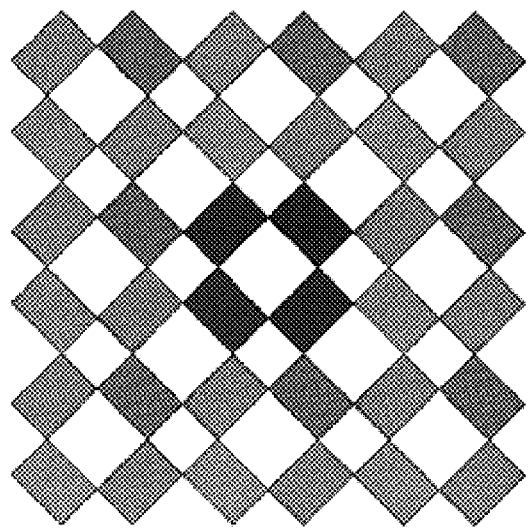
Figure 7C:
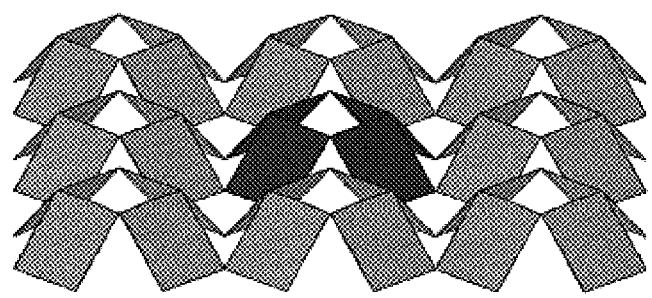

In the presence of different templates, it is also possible to obtain very different supramolecular isomers. These are represented by the formula $Cu_2(pyridine)_2(O_2CR)_4$ SBUs. An example of this, $[Cu_2(pyridine)_2(bdc)_2]_n$, is shown in FIGS. 7A–7C. In this embodiment, a "pseudo-square grid" structure is formed from four SBUs to make a bowl-shaped nanoscale SBU. This bowl shape is the same type of shape having the curvature as in the previous structures, but since only four SBUs are used, the entire sphere is not formed. In this structure, as in the previous ones, the bridging bdc moieties orient to form the observed polymeric structure.

EXAMPLE 5

Additional Discrete Spheric Crystal

Procedure: 0.2326 g $Cu(NO_3)_2.2.5H_2O$ (copper nitrate hemipentahydrate) (1 mmol) was dissolved in 5 ml of methanol and 3 ml of nitrobenzene. The second solution contained 0.166 g (1 mmol) of 1,3-bdc dissolved in 5 ml of methanol and 0.3 ml of 2,6-dimethylpyridine (3 mmol). Slow diffusion of the second solution over the Cu-containing solution produced greenish-blue crystals.

Analysis: Crystallography: a=33.8617, b=36.8416, c=29.5142, $\beta$=93.456, space group: C2/c, Volm=36752.45.

EXAMPLE 6

Additional Discrete Spheric Crystal

Procedure: 0.2326 g of $Cu(NO_3)_2.2.5H_2O$ (1 mmol) was dissolved in 5 ml of methanol and 4 ml of nitrobenzene. The second solution was prepared from 0.166 g (1 mmol) of 1,3-bdc dissolved in 5 ml of methanol and 0.3 ml of 2,6-dimethylpyridine (3 mmol). After slow diffusion of the second solution over the first solution, greenish-blue crystals were formed.

Analysis: Crystallography: a=28.2457, b=28.2457, c=28.6669, $\gamma$=120°, space group: $P6_3/m$, Volm=19806.87.

EXAMPLE 7

Additional Discrete Spheric Crystal

Procedure: 0.093 g $Cu(NO_3)_2.2.5H_2O$ (4 mmol) was dissolved in 5 ml of methanol and 3 ml of nitrobenzene. The second solution was made from 0.066 g (4 mmol) of 1,3-bdc dissolved in 5 ml of methanol and 0.12 ml of 2,6-dimethylpyridine (1.2 mmol). Again, diffusion of the second solution over the first produced greenish-blue crystals.

Analysis: Crystallography: a=b=c=27.6895, space group: I m–3 m, Volm=21203.03.

Figure 9:
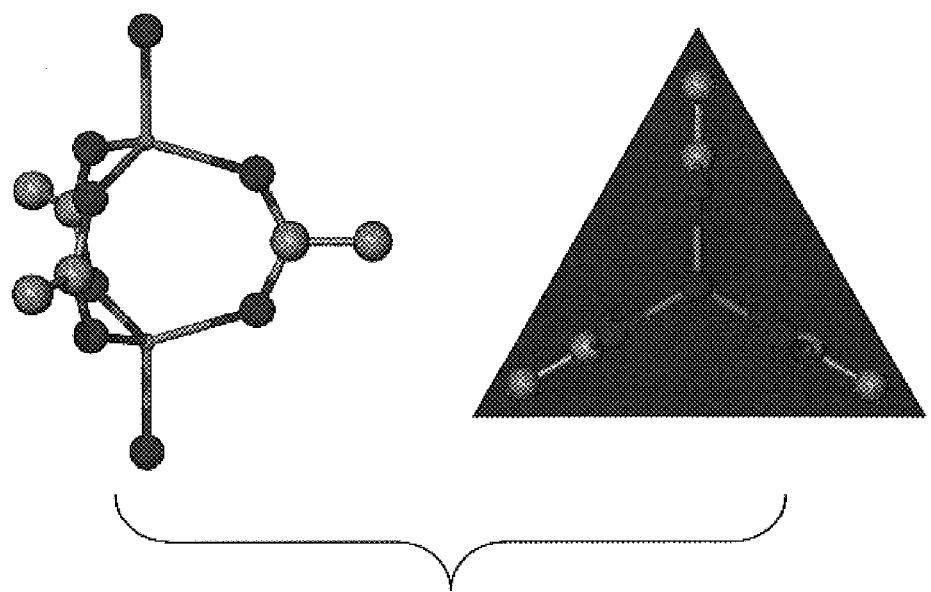
FIG. 9 shows a further embodiment of the invention, a triangular (nSBU).

In addition to crystals derived from square SBUs, structures having SBUs that generate triangular shapes are also within the scope of the instant invention, as shown in FIGS. 9A and 9B. Whereas the SBU that generates the square is represented by $M_2(RCO_2)_4$, SBUs of the general formula $M_2(RCO_2)_3$ generate structures having triangular shapes. Again, M and R can be selected from the groups already stated. Examples of some of these shapes are shown in FIGS. 10A–10I, but other possibilities, as is readily ascertainable by those of ordinary skill in the art, are also herein contemplated. Representations of these structures are shown in FIGS. 11A–11F and FIGS. 15A–15F, and the porosities and packing of these structures are also depicted. The basic schematic for FIGS. 11A–11F is $\{[XL_2Zn_2(btc)_{1.333}]_3\}_n$, where L=pyridine or water, and $X=NO_3^-$. The schematic representation for FIGS. 15A–15F is $\{[L_2Zn_2(btc)_{1.333}]_{12}\}_n$, where L=water or pyridine again.

Another group of compounds is also derived from complexes of the angular trifunctional ligand benzene-1,3,5-tricarboxylate.

Referring again to FIGS. 11A–11F, the crystal structure of the compound reveals that it is composed of molecular squares and triangles that were formed by self-assembly into small cubicuboctahedra because two of the btc carboxylate moieties impose a 120° angle at the linkage between the polygons. These have six square faces and eight triangular faces, and the small cubicuboctahedra are fused with one another at the square faces because of the presence of the third carboxylate of each btc ligand. Thus, each square face is fused or shared with the square face of an adjacent small cubicuboctahedron, whereas each triangular face is linked to squares in such a manner that another, smaller polyhedron is generated. This smaller polyhedron is one of the other faceted polyhedra that can be sustained by vertex-linked triangles, which defines an octahemioctahedron. The framework exhibited is low density because the faceted polyhedra are inherently open and, therefore, define a porous structure.

Figure 12A:
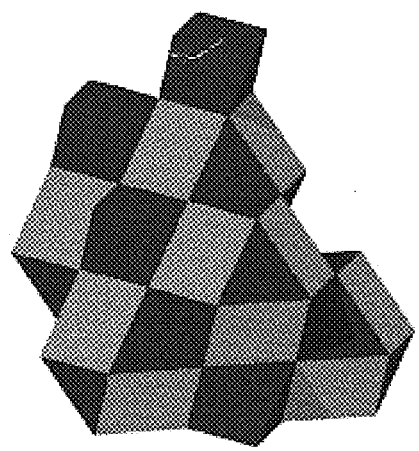
FIGS. 12A–12C show schematic illustrations of three uniform space filling models based on Platonic and Archimedean polyhedra that are possible for faceted polyhedra.
Figure 12B:
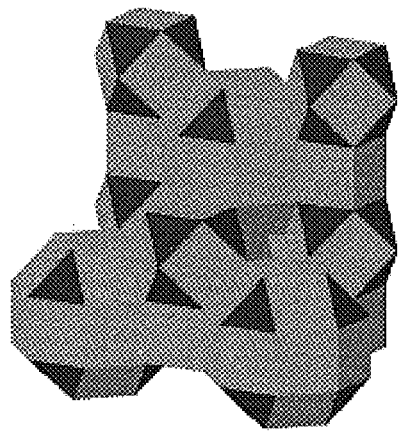
Figure 12C:
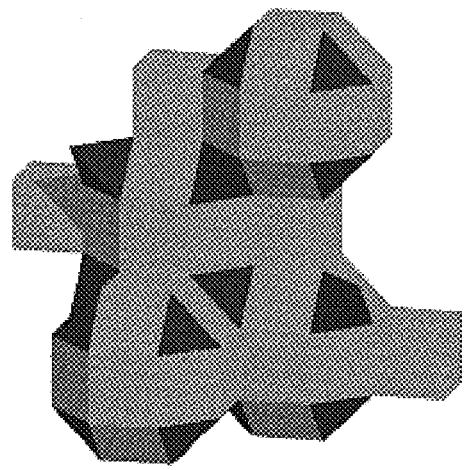

An aspect of these uniform polyhedra that makes them desirable as nanoscale building blocks is that there is inherently a great deal of control concerning the framework geometries that they must adapt if they close-pack. For example, for combinations of Platonic and Archimedean polyhedra, there exist only eleven possible space-filling infinite frameworks. In addition, there are even greater restrictions for faceted polyhedra since they must pack such that each polygon is connected only by its vertices and does not share its edges. Indeed, the possible packing for faceted polyhedra is restricted to only three related space-filling architectures as shown in FIGS. 12A–12C: rhombicuboctahedra/cuboctahedra/cubes (1:1:3), as FIG. 12A; rhombicuboctahedra/cubes/tetrahedral (1:1:2), FIG. 12B; cuboctahedra/octahedral (1:1), FIG. 12C.

Figure 13A:
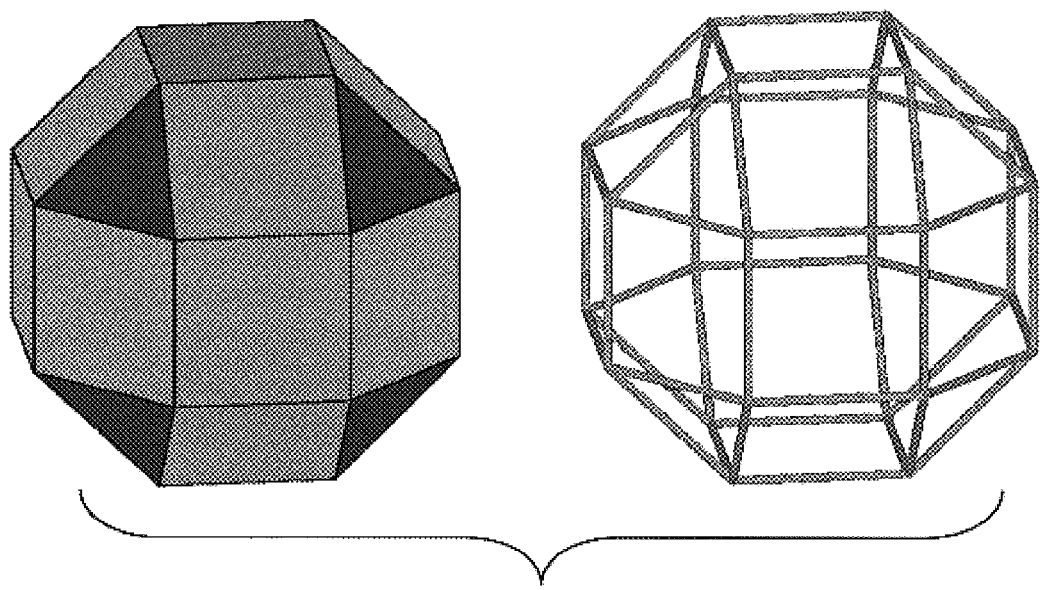
FIGS. 13A and 13B show a schematic illustration of how the small cubicuboctahedron and the small rhombihexahedron have a congruent edge-skeleton with the Archimedean polyhedron, the rhombicuboctahedron.
Figure 14A:
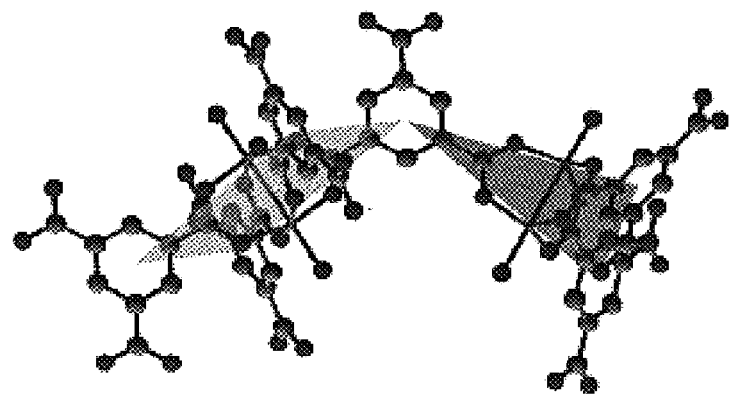
FIGS. 14A and 14B show an illustration of how the vertices of the molecular squares and triangles are connected by the benzene tri-carboxylic moieties. Molecular squares and triangles are shown in FIG. 14A. Only molecular squares are shown in FIG. 14B.
Figure 14B:
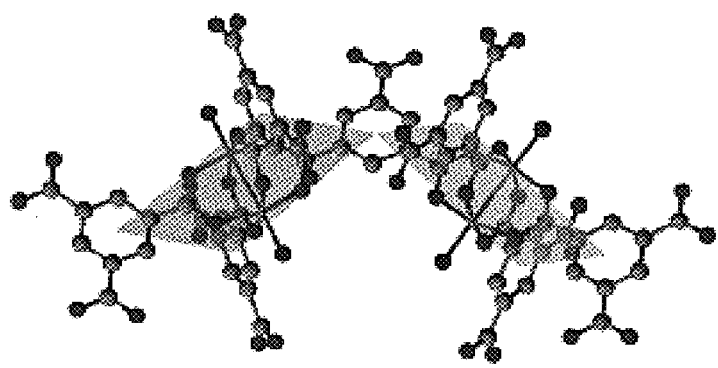
Figure 15A:
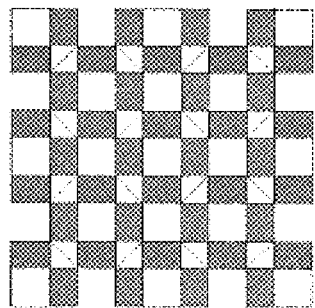
FIGS. 15A–15F show another polyhedra formed containing zinc as the metal in the structure.
Figure 15B:
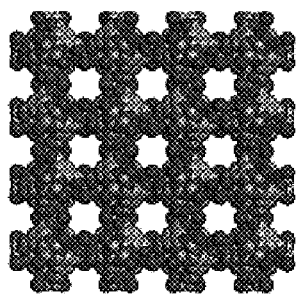
Figure 15C:
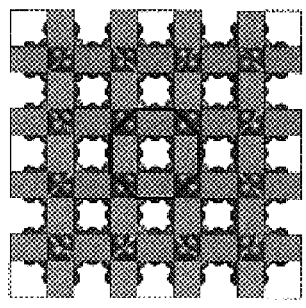
Figure 15D:
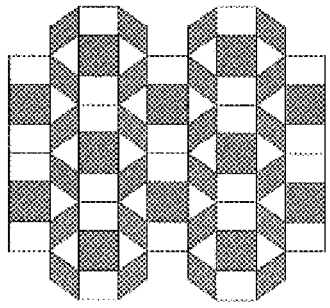
Figure 15E:
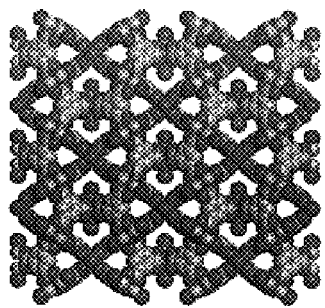
Figure 15F:
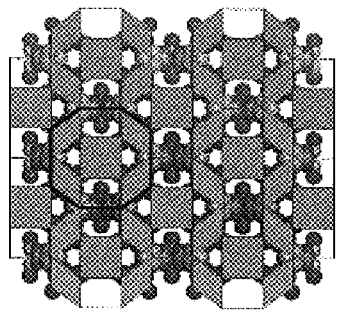

Since the small cubioctahedron has a congruent edge-skeleton with a rhombicuboctahedron, as depicted in FIG. 13A, it must adapt one of only two possible frameworks. Furthermore, only one of these frameworks can sustain vertex-only connected triangles and squares. It therefore follows that self-assembly of small cubicuboctahedra, or alternately, self-assembly of triangles and squares by vertex sharing, can result in only one framework. The structure therefore is pre-ordained and, furthermore, is clearly prototypal for other frameworks that can be formed from other molecular triangles and squares. The dimensions of the small cubicuboctahedron are the same as the unit cell dimensions as there is only one small cubicuboctahedron per unit cell. The separation between opposite square faces is therefore 2.05 nm and the dimensions of the windows are approximately 0.9 nm. The overall structure contains channels and cavities that are entirely predictable based on the dimensions of the constituents. It is also noted that the dihedral angle of 125° 16' would exist in a perfect small cubicuboctahedron, as shown in FIGS. 14A and 14B.

EXAMPLE 8

Synthesis of a Discrete Crystal (OH-nanoball)

An OH-nanoball synthesized from the 120 degree dicarboxylate ligand shown in FIG. 2B is described below.

Synthesis: 5 g of 5-hydroxyisophthalic acid (27.5 mmol) and 6.39 g of copper nitrate hemipentahydrate (27.5 mmol) was dissolved in methanol (100 ml). 6.40 ml of lutidine (54.9 mmol) was added and the solution was stirred for 15 min under ambient conditions. Addition of diethylether (120 mL) to the solution resulted in precipitation of crude material (10.573 g), crystallization of which from dimethyl sulfoxide afforded the title compound.

Crystal data: Intensity data collected at 200 K. Tetragonal, space group I4/mmm, a=b=31.111(4), c=35.999(6) Å, V=34844(8) Å$^3$, Z=2, D$_c$=0.708 g cm$^{-3}$, $\mu$=0.778 mn$^{-1}$, F(000)=7366, 2θmax=42.08°(−30≧h≧31, −31≧k>31, −36≧l>21). Final residuals (for 296 parameters) were R1=0.1531 for 5170 reflections with I>2σ(I), and R1=0.2128, wR2=0.4702, GOF=1.679 for all 49928 data. Residual electron density was 1.051 and −0.592 e Å$^{-3}$.

XPD: Broad peaks

TGA: Complex weight losses at 36.09, 136.31, 257.14, 334.46, 599.61° C.

IR (neat, cm$^{-1}$): 3217.73 (s, OH), 1633.73 (s, carboxylate), 1380.33 (s, carboxylate)

Solubility: Readily soluble in methanol, ethanol, isopropanol and sparingly soluble in DMF and DMSO.

EXAMPLE 9

Synthesis of a Discrete Crystal (NO$_2$-nanoball)

An NO$_2$-nanoball synthesized from the 120 degree dicarboxylate ligand shown in FIG. 2C is described below.

Synthesis: Slow diffusion of 1 ml methanolic solution of 5-nitroisophthalic acid (0.2 M) and Cu(NO$_3$)$_2$.2.5 H$_2$O (0.2 M) into 1 ml methanolic solution lutidine (0.4M) yielded blue square crystals.

Crystal data: crystals do not diffract (indicative of nanoball structure).

XPD: Broad peaks (indicative of nanoball structure).

EXAMPLE 10

Synthesis of a Discrete Crystal (larger sphere)

Figure 3A:
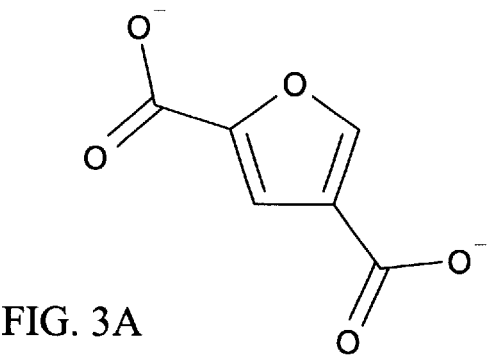
FIGS. 3A–3G illustrate representative ligands for 144°.
Figure 3B:
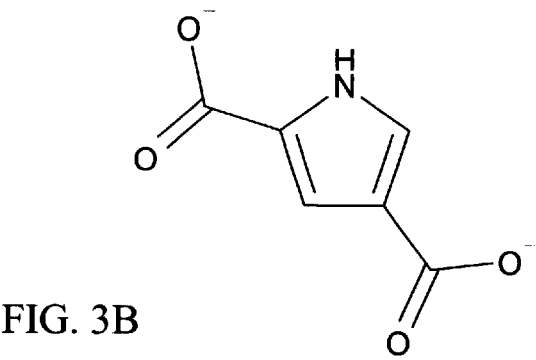
Figure 3C:
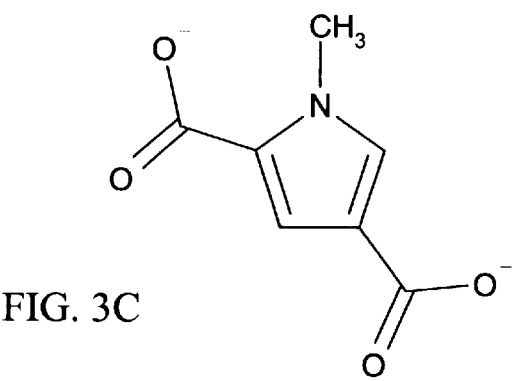
Figure 3D:
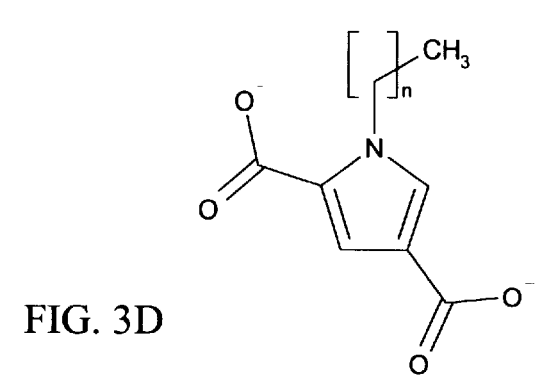
Figure 3E:
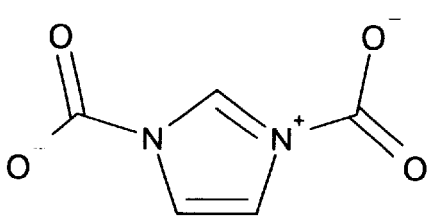
Figure 3F:
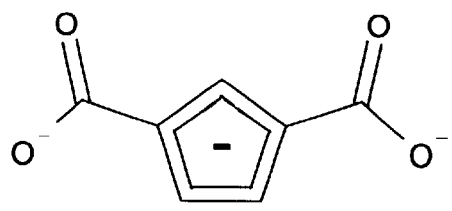
Figure 3G:
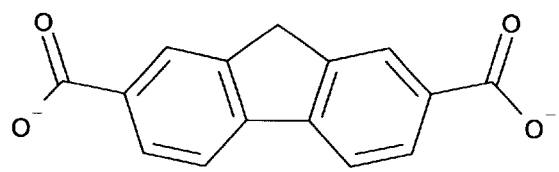

A larger nanoball synthesized from the 144 degree dicarboxylate ligand shown in FIG. 3C is described below.

Procedure. 244 mg Cu(NO$_3$)$_2$.2.5H$_2$O in 5 mL methanol was added to 165 mg N-methylpyrrole-2,4-dicarboxylic acid and 1 mL pyridine in 5 mL methanol. The solution was sealed and left under ambient conditions. Prismatic blue crystals formed within several days.

Crystal data: crystals do not diffract (indicative of nanoball structure).

XPD: Broad peaks (indicative of nanoball structure).

EXAMPLE 11

Growth of Nanoballs on a Surface

Because the nanoballs of the subject invention are highly soluble in common organic solvents such as methanol, ethanol, l-propanol, DMF, and hot acetonitrile, the microcrystals are suitable for growth on substrates such as mica or glass. This was confirmed by atomic force microscopy (AFM), which is known in the art as a widely used tool for the study of crystal growth and behavior on surfaces. Examples of data obtained include: size control of nanocrystals on Langmuir-Blodgett films, protein crystal growth, molecular and nano-tribology, statistical analysis of 2D crystal sizes, dopant effects on crystal growth, and annealing effects on crystallization. These AFM studies revealed that the microcrystals are of quite uniform dimensions and that they are stable even after mild heating.

Nanoballs were synthesized from the acid shown in FIG. 2B and deposited on mica and glass substrates. AFM images of the products obtained for the mica surface, without thermal annealing, show increasing density of microcrystals with increasing concentration. The microcrystals had an average height of 140 nm with a variation of 30 nm; the surface roughness (root-mean-square; RMS) was 56 nm. The average size was 1.3 μm with a variation of 0.4 μm.

Figure 25:
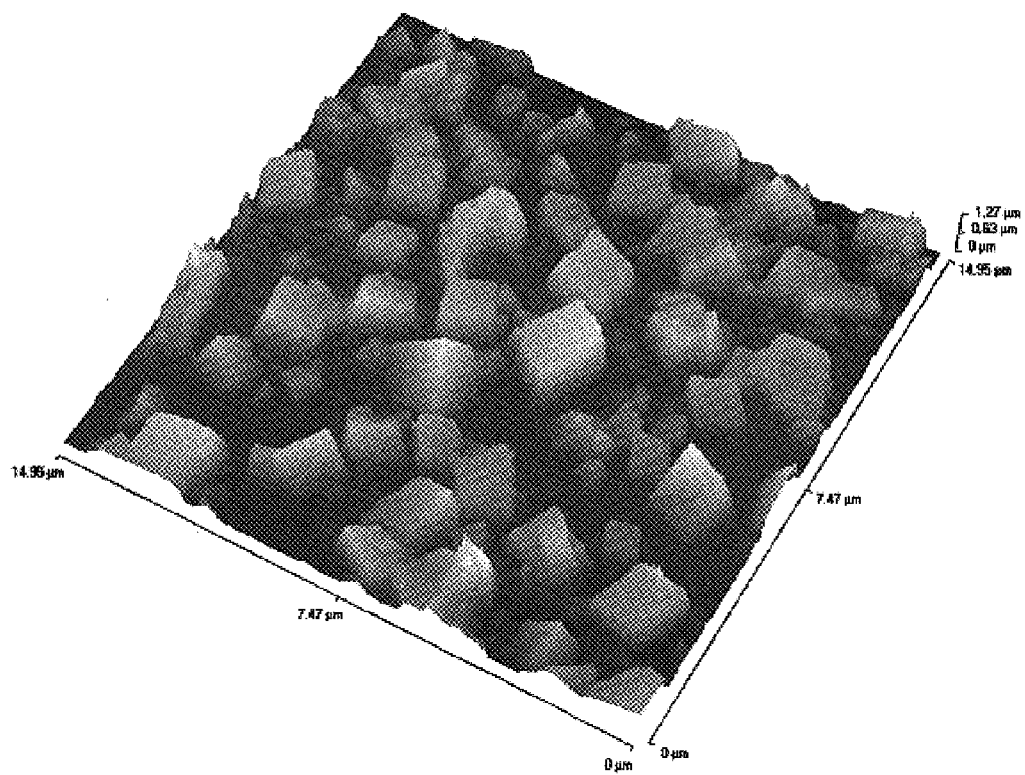
FIG. 25 shows an AFM image of microcrystals on glass after annealing at 37° C. for 24 hours.
Figure 26:
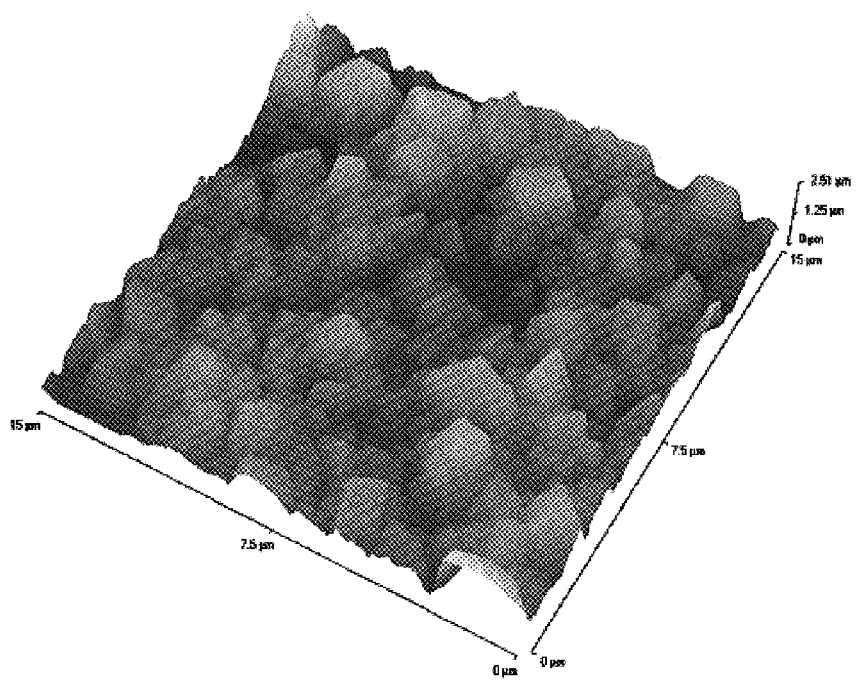
FIG. 26 shows an AFM image of microcrystals on glass after annealing at 75° for 24 hours.

In the case of films prepared on glass, observation on samples that were not thermally treated gave poor image quality even in the non-contact mode due to the presence of residual solvent forming a strongly bound contamination film. This contamination layer was removed by heating to 37° C. or 75° C. over 24 hours. AFM images of microcrystals on glass after annealing at 37° C. and 75° C. are shown in FIG. 25 and FIG. 26, respectively.

As shown in the figures, the roughness (RMS) is 236 and 261 nm. Image analysis shows an average size of 1.4 μm for the sample annealed at 37° C. and again 1.4 μm for that annealed at 75° C., with the variances being 0.4 μm. The average heights were 500 and 600 nm, respectively. For the 37° C. sample, the height values were randomly distributed about the average, but in the case of the 75° C. sample, there was an apparent statistical distribution of heights at 300, 600, and 900 nm.

EXAMPLE 12

A Square Lattice Formed From Square SBUs

Procedure: 0.2326 g $Cu(NO_3)_2 \cdot 2.5H_2O$ (1 mmol) was dissolved in 4 ml of water. An additional solution was made by dissolving 0.166 g (1 mmol) of 1,3-bdc in 4 ml of ethanol and 0.24 ml or pyridine (3 mmol). Green crystals were obtained after slow diffusion of the 1,3-bdc solution over the $Cu(NO_3)_2 \cdot 2.5H_2O$.

Analysis: Crystallography: a=18.7912, b=128.7912, c=16.8886, space group: P4/ncc, Volm=5963.5

TGA: around 25% weight loss before decomposition at around 280° C.

IR spectrum: intense peak at 1381 $cm^{-1}$

XPD: sharp high peak at below 10° in 2θ and some other distinct peaks at above 10° in 2θ

Solubility: sparingly soluble in common organic solvents.

Figure 8A:
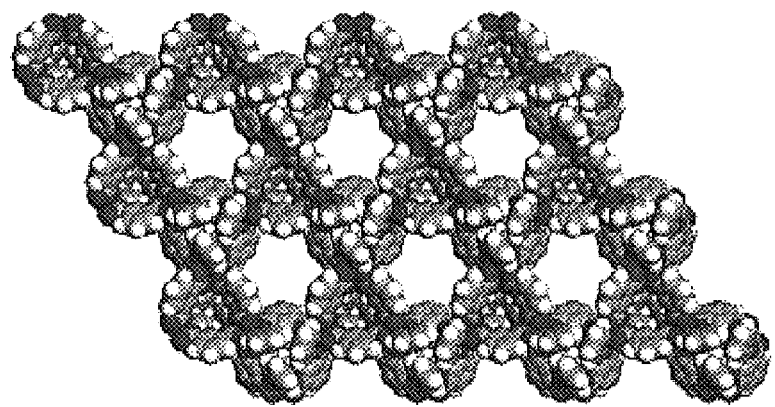
FIGS. 8A–8C show space-filling and schematic representations of the arrangement of triangular nSBUs in the nanoscale Kagomé lattice structure described in Example 15.
Figure 8B:
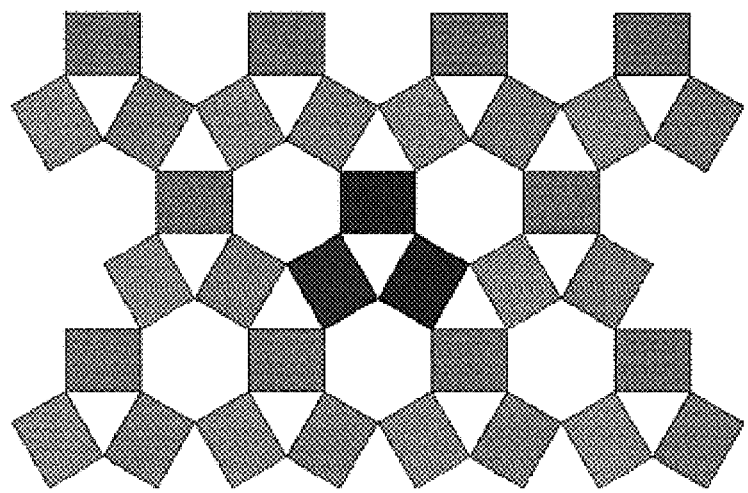
Figure 8C:
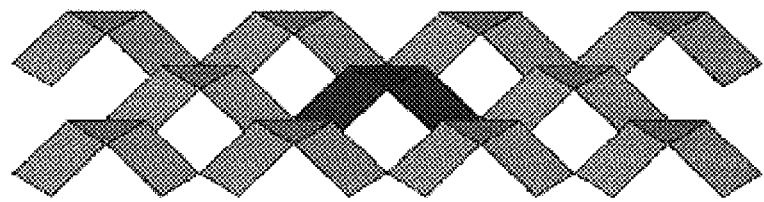

An additional embodiment based on the bowl-shaped nanoscale with triangular SBUs is shown in FIGS. 8A–8C. Again, the generic formula $[Cu_2(pyridine)_2(bdc)_2]_n$ applies, but the structure corresponds to a semi-regular tiling pattern based on triangles and hexagons, since instead of four units as above, three are used in this case. Because of the nature of the bowl-shaped SBUs and the required connectivity, the hexagons are open and the 2D sheets pack in an eclipsed manner. Large solvent channels (1.35 nm in diameter) therefore exist parallel to the 2D sheet.

EXAMPLE 13

A Kagomé Lattice Formed from Triangular SBUs

Procedure: 0.2326 g $Cu(NO_3)_2 \cdot 2.5H_2O$ (1 mmol) was dissolved in 6–7 ml of methanol, and then 0.256 g of naphthalene (2 mmol) was also dissolved in the same solution. A second solution containing 0.166 g (1 mmol) of 1,3-bdc dissolved in 6–7 ml of methanol and further containing 0.3 ml of 4-picoline (3 mmol) was prepared. Slow diffusion of the second solution over the first produced green crystals.

EXAMPLE 14

Additional Kagomé Lattice Formed from Triangular SBUs

Procedure: 0.2326 g $Cu(NO_3)_2 \cdot 2.5H_2O$ (1 mmol) was dissolved in 6–7 ml of ethanol. Then 2–3 ml of nitrobenzene was added to that solution. A second solution containing 0.166 g (1 mmol) of 1,3-bdc dissolved in 6–7 ml of ethanol with 0.24 ml of pyridine (3 mmol) was prepared. Again slow diffusion of the second solution over the first yielded green crystals.

Analysis of Examples 12 and 13: Crystallography: a=18.6001, b=18.6001, c=26.2181, γ=120, space group: R32, Volm: 7855.29; a=18.62, b=18.62, c=19.804, γ=120, space group: P3c1, Volm: 5956.672

TGA: around 27% weight loss before decomposition at around 250° C.

IR spectrum: intense peak at 1382 $cm^{-1}$

XPD: broad XPD pattern has been observed

Solubility: sparingly soluble in common organic solvents

It was also found that substitution of 2,6-dimethylpyridine for the pyridine produced similar results. These are described in Examples 5–7 and the structures obtained were the same as observed for the other square-based spheres.

EXAMPLE 15

Additional Kagomé Lattice Formed from Triangular SBUs

Procedure: Slow diffusion of ethanolic copper (II) nitrate into a solution of bdc and pyridine in ethanol in the presence of an appropriate template (nitrobenzene, 1,2-dichlorobenzene or naphthalene) affords prismatic blue-green crystals of $[(L_2Cu_2(bdc)_2)_3]_n$.

An ethanolic solution (7 ml) containing 166 mg 1,3-$C_6H_4$ $(CO_2H)_2$ (1.00 mmol) and 0.24 ml $C_6H_5N$ (2.97 mmol) was carefully layered onto an ethanolic solution (7 ml) containing 232 mg $Cu(NO_3)_2 \cdot 2.5H_2O$ (1.0 mmol) and an appropriate template (i.e., 3 ml $C_6H_5NO_2$, 3 ml dichlorobenzene (1,2-$C_6H_4Cl_2$), or 5 mg $C_{10}H_8$). The solutions were left to mix by slow diffusion, and small bluish-green hexagonal crystals formed within days.

It should be understood that use of a template is optional. For example, the procedure described above can be carried out without a template under similar conditions as those of Example 10, without the addition of naphthalene.

The crystal structure as shown in FIGS. 8A–8C can be described as the result of self-assembly of triangular nSBUs to yield a nanoscale Kagomé lattice. $Cu_2$ dimers are positioned at the lattice points and are bridged via the bdc ligands, thereby generating large hexagonal cavities within the layer. The bowl-shaped nSBU facilitates efficient packing when the bowls are eclipsed, which results in eclipsing of the hexagonal cavities (0.91 nm effective diameter) and hexagonal channels of the same dimension. The layers are undulating due to the curvature imparted by the bdc moiety, have a 1.24-nm amplitude and overlap with adjacent layers by approximately 20%. The apical positions of the $Cu_2$ dimers are occupied by coordinated pyridine ligands, and highly disordered solvent molecules occupy the hexagonal channels (ca. 28% by weight). Thermal analysis (TGA/DSC) suggested that the included solvent and the pyridine ligands could be removed at ca. 200° C., and that the desolvated lattice is thermally stable to temperatures in excess of 300° C. The most intense peaks observed in X-ray powder diffraction (XPD) patterns from the bulk sample are consistent with those calculated from single crystal data.

EXAMPLE 16

Additional Square Lattices Formed From Square SBUs

Figure 23:
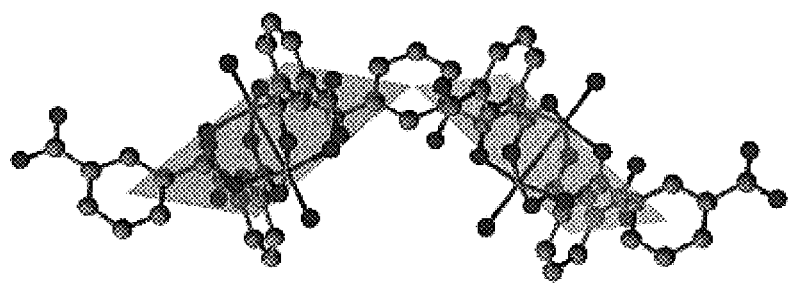
FIG. 23 shows an example of the conformation of a bdc ligand that produces 2D networks (square and Kagomé) of the subject invention.

By variation of the crystallization conditions a phase based on square nSBUs, having the formula $[L_2Cu_2(bdc)_2]_4]_n$, was obtained. An example of the conformation of a bdc ligand that produces 2D networks (square and Kagomé) of the subject invention is shown in FIG. 23.

Figure 20A:
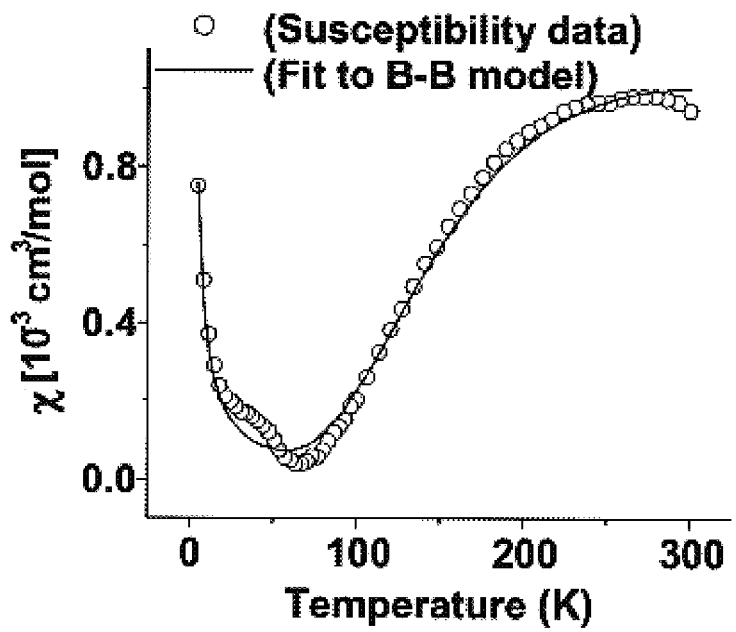
FIGS. 20A and 20B show the magnetic properties of the structure described in Example 15.
Figure 20B:
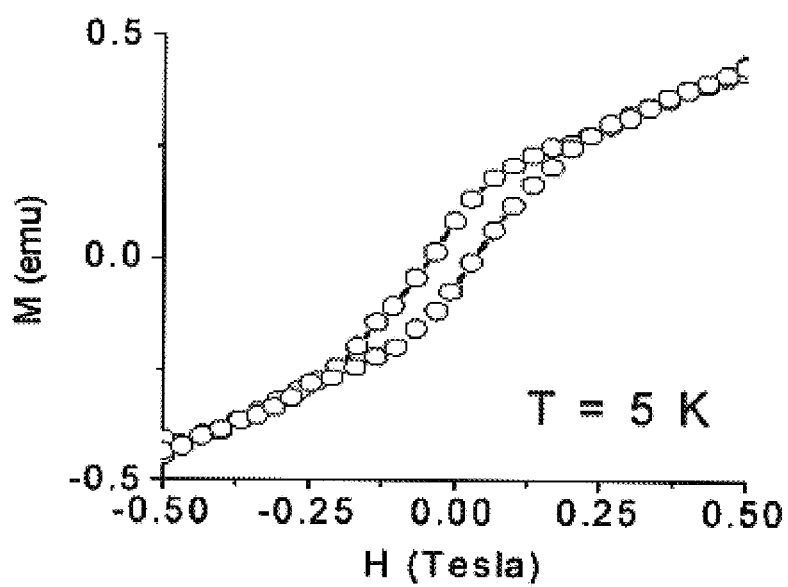

The magnetic properties of the structure described in Example 15 are shown in FIGS. 20A and 20B. FIG. 20A shows the temperature-dependent susceptibility ($\chi$) at a constant field (H=0.1 Tesla) and FIG. 20B shows the field-dependent magnetization at low temperature (T=5 K). The data exhibit rich structure that can be associated with the combined intra-dimer and inter-dimer magnetic interactions. Cooperative magnetism in $Cu_2$ dimer-based complexes has been studied in the past and known to predominantly exhibit antiferromagnetic coupling (Jotham, R. W. et al. [1972] *Dalton Trans.* pp. 428–438; Kato, M. et al. [1964] *Chem. Rev.* 64:99–148).

The temperature-dependent $\chi$ in FIG. 20A shows a maximum just below 300K and a minimum at around 60K followed by an upturn at lower temperature. The data presented has been corrected for the diamagnetic contribution. The $\chi$-T variation is consistent with cooperative magnetic behavior observed in dimeric copper complexes. A standard Bleaney-Bowers (BB) model (Bleaney, B. et al. [1952] *Proc. R. Soc. London, A* 214:451–465) was used to generate a fit and this is also shown in FIG. 20A. The two main fit parameters are the intra-dimer (J) and inter-dimer (J') interaction terms. From this fit, the values of J=−350 cm$^{-1}$ and J'=−18 cm$^{-1}$ were obtained. This model also takes into account the presence of uncompensated moments that follow a Curie law. This accounts for the upturn in susceptibility for temperatures below 50K.

A clue as to the nature of the geometrically frustrated antiferromagnetic state for this compound is revealed in the M-H data shown in FIG. 20B. A well-defined hysteresis loop was observed indicative of ferromagnetic behavior. The presence of hysteresis even at 300K was also confirmed. It has thus been demonstrated herein that, in accord with the subject invention, it is possible to arrange nanoscale molecular objects (not atoms) with precise control and achieve periodic magnetic nanostructures (Sun, S. H. et al. [2000] *Science* 287:1989–1992).

Within the context of the triangular Kagome lattice, we can now attempt to understand the origin of the ferromagnetic-like response leading to magnetic hysteresis. The triangular lattice framework will result in disruption of perfect antiferromagnetic ordering by introducing spin frustration that leads to canted arrangement of spins. Of course, here the term spins refers to the moments of the individual dimers. Spin canting can lead to the appearance of effective weak ferromagnetic long-range order. It has also been pointed out that in low dimensional systems such as semi-conductor quantum dots, molecular magnets etc., electron correlation effects in an antiferromagnetic lattice can lead to flat-band ferromagnetism (Tamura, H. et al. [2001] *Phys. Status Solidi B* 224:723–725).

Figure 21A:
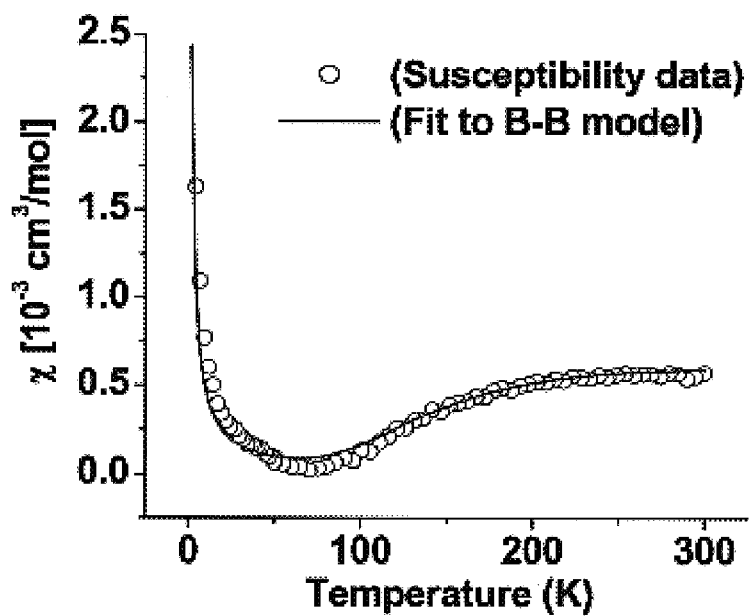
FIGS. 21A and 21B show the magnetic properties of Example 16.
Figure 21B:
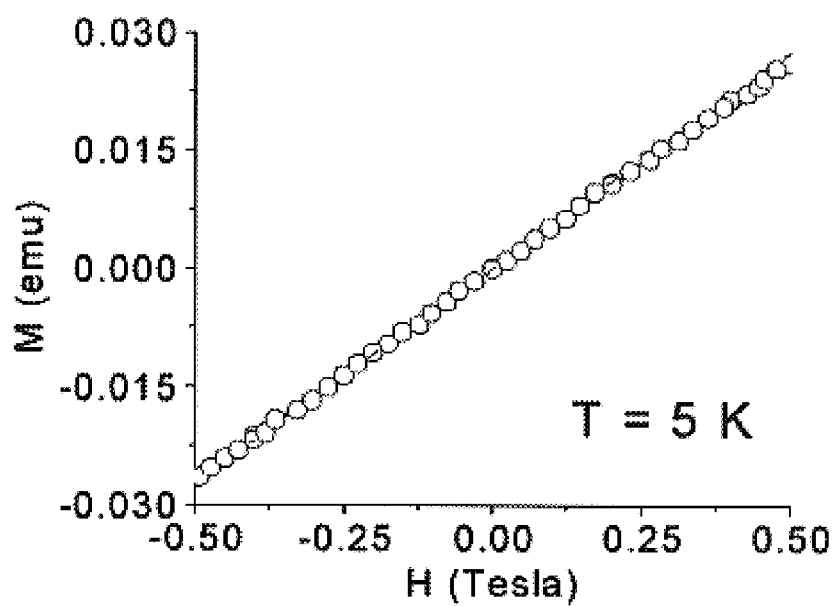

The structure described in Example 13 exhibits a different topology, the 2D square lattice that is shown in FIGS. 7A–7C. In this case, from geometry considerations, spin frustration is ruled out and this is reflected in the magnetic measurements shown in FIGS. 21A and 21B. To keep the comparison direct and simple, the $\chi$-T and M-H data has been plotted using identical conditions as that of FIGS. 20A and 20B. These magnetic data are very similar to recent experimental results reported by other groups on $Cu_2$ dimeric complexes (Zhang, X. X. et al. [2000] *J. Appl. Phys.* 87:6007–6009). Theoretical fit using the BB model to the $\chi$-T data in this case yields fit parameters, J=−380 cm$^{-1}$ and J'=−85 cm$^{-1}$. Of course, the striking feature is the lack of hysteresis for this system with the M-H data exhibiting a straight line representative of a more traditional paramagnetic behavior.

These results dramatically underscore the potential afforded by supramolecular chemistry for the design of molecular nanostructure assemblies with desirable physical properties and emphasize how the composition of a material is not the only feature one must consider when designing a phase that exhibits molecular magnetism.

EXAMPLE 17

Polymers Based on Small Cubicuboctahedra

Procedure: A 10-ml solution of $Zn(NO_3)_2 \cdot 2H_2O$ (220 mg; 0.741 nmol) and 1,3,5-benzenetricarboxlic acid (220 mg; 1.05 mmol) in methanol was layered onto a 10-ml solution of nitrobenzene containing 0.23 ml of pyridine (2.8 mmol). Large single crystals formed within hours under ambient conditions.

EXAMPLE 18

Polymers Based on Small Rhombihexahedra

Procedure: A 10-ml solution of $Zn(NO_3)_2 \cdot 6H_2O$ (202 mg; 0.679 mmol) and 1,3,5-benzenetricarboxylic acid (126 mg; 0.6 mmol) in methanol was layered onto a 10-ml solution of benzene containing pyridine (0.1 ml; 1.24 mmol). Large single crystals formed within hours under ambient conditions.

Figure 13B:
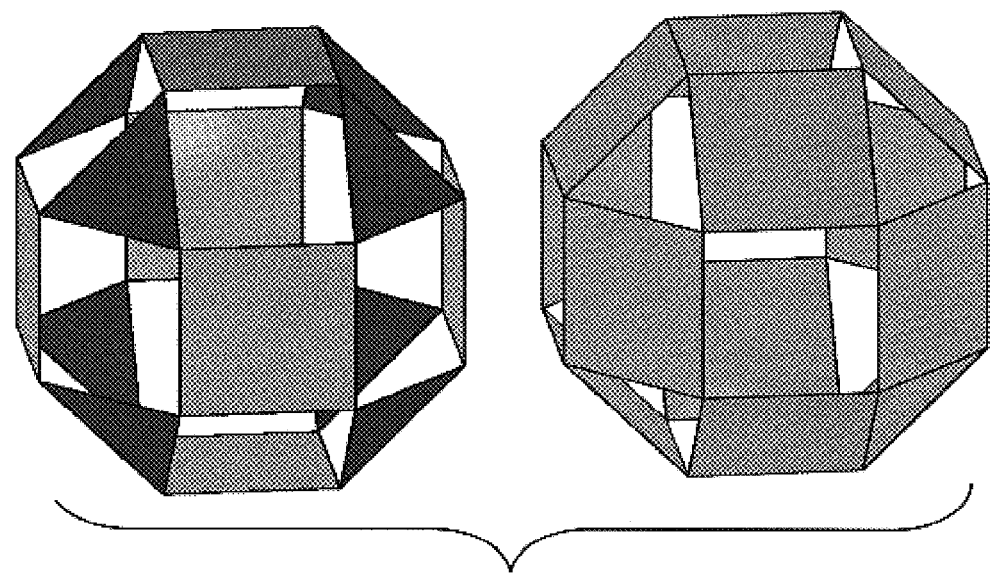

The crystal structure of Example 15, as illustrated in FIGS. 15A–15F, reveals a compound that consists of small rhombihexahedra, which have congruent edge-skeletons with the rhombicuboctahedron (FIGS. 13A and 13B), that are fused at the square faces. There is only one possible space-filling arrangement that generates a close-packed framework for these polyhedra, a structure that must be based on squares alone, dihedral angles of 120° (FIG. 14B), and the rhombicuboctahedron edge-skeleton: rhombicuboctahedra/cubes/tetrahedral (1:1:2), shown in FIG. 12B. The small rhombihexahedron of Example 15 is slightly larger than the polyhedron of Example 14. It has a diameter of 2.3 nm, and the triangular windows have dimensions of approximately 0.9 nm.

The thermal stabilities of both Examples 14 and 15 appear to be consistent with their structures and molecular components. Crystals of the compounds appear stable indefinitely when in contact with mother liquor. Weight losses of 7.2 and 8.2%, respectively, are consistent with loss of methanol, which occurs under ambient conditions, and the samples remain crystalline, as confirmed by single crystal diffraction patterns. Greater weight losses and irreversible decomposition occurs upon heating and corresponds to further loss of methanol and pyridine molecules. The interconnectivity of the cavities in both structures is quite different, but the windows and free volume of the dissolved structures are similar.

In a further embodiment, spin-frustrated lattices were formed, these representing an attractive target that was found to exemplify the antiferromagnetic Kagomé lattice. This example of a nanoscale Kagomé lattice is a phase that is sustained by paramagnetic dicopper(II) spin pairs (metal dimers) positioned at the lattice point. One advantage of this particular phase is that it exploits the concept of self-assembly of nanoscale secondary building units, or nSBUs, and therefore offers a versatile system for which the effect of systematically substituting the molecular components can be evaluated.

As described above, the structures of the instant invention are useful in any application in which liquid crystals are used, for example, and particularly in which magnetic properties are desirable, such as for use in magnetic devices or other applications. In addition, the instant molecules can be used in conjunction with pharmaceuticals as adjuvants or carriers. Other uses include optoelectric materials, lubricants, catalysts, polymer additives, and any other material where liquid crystals are used.

What is claimed is:

1. A faceted polyhedron molecule comprising polygon moieties and linking moieties, wherein said polygon moieties comprise edges and vertices, wherein a first polygon moiety is attached to a second polygon moiety by at least one of said linking moieties, and wherein said at least one linking moiety is attached to a vertex of said first polygon moiety and a vertex of said second polygon moiety; wherein the faceted polyhedron molecule is a discrete macromolecule.

2. The faceted polyhedron molecule of claim 1, wherein said at least one linking moiety is a coordinating ligand or a bridging ligand.

3. The faceted polyhedron molecule of claim 2, wherein said first polygon moiety and said second polygon moiety each comprise a metal, and wherein said linking moiety is a coordinating ligand.

4. The faceted polyhedron molecule of claim 3, wherein said coordinating ligand is attached to said vertex of said first polygon moiety and said vertex of said second polygon moiety through covalent interactions.

5. The faceted polyhedron molecule of claim 3, wherein said coordinating ligand is a multifunctional carboxylate ligand.

6. The faceted polyhedron molecule of claim 5, wherein said multifunctional carboxylate ligand is a bifunctional carboxylate ligand.

7. The faceted polyhedron molecule of claim 6, wherein said bifunctional carboxylate ligand is benzene-1,3-dicarboxylate.

8. The faceted polyhedron molecule of claim 1, wherein said linking moiety is a trifunctional carboxylate ligand.

9. The faceted polyhedron molecule of claim 8, wherein said trifunctional carboxylate ligand is 1,3,5-benzene tricarboxylate.

10. The faceted polyhedron molecule of claim 1, wherein said linking moiety subtends an angle of about 90° between the planes occupied by said first and second polygon moieties.

11. The faceted polyhedron molecule of claim 1, wherein said linking moiety subtends an angle greater than about 90° between the planes occupied by said first and second polygon moieties.

12. The faceted polyhedron molecule of claim 1, wherein said linking moiety subtends an angle of about 120° between the planes occupied by said first and second polygon moieties.

13. The faceted polyhedron molecule of claim 1, wherein said linking moiety subtends an angle of about 144° between the planes occupied by said first and second polygon moieties.

14. The faceted polyhedron molecule of claim 1, wherein at least one of said first and second polygon moieties comprises a non-metal.

15. The faceted polyhedron molecule of claim 1, wherein said first or second polygon moiety can sustain 3-fold rotational symmetry.

16. The faceted polyhedron molecule of claim 1, wherein said first or second polygon moiety can sustain 4-fold rotational symmetry.

17. The faceted polyhedron molecule of claim 1, wherein at least one of said first and second polygon moieties comprises a transition metal.

18. The faceted polyhedron molecule of claim 17, wherein said transition metal is in a 2+ transition state.

19. The faceted polyhedron molecule of claim 17, wherein said first and said second polygon moieties each comprise transition metals.

20. The faceted polyhedron molecule of claim 17, wherein said first and second polygon moieties each comprise transition metals, and wherein said transition metals are not in the same transition state.

21. The faceted polyhedron molecule of claim 16, wherein said transition metal is not in a 2+ transition state, and wherein said faceted polyhedron molecule further comprises a counterion that may or may not be coordinated to said transition metal.

22. The faceted polyhedron molecules of claim 1, further comprising a solvent molecule.

23. The faceted polyhedron molecule of claim 1, further comprising a solvent molecule selected from the group consisting of methanol, ethanol, 1-propanol, dimethylformamide, and acetonitrile.

24. A compound comprising a faceted polyhedron molecule, wherein said faceted polyhedron molecule comprises polygon moieties and linking moieties, wherein said polygon moieties comprise edges and vertices, wherein a first polygon moiety is attached to a second polygon moiety by at least one of said linking moieties, wherein said at least one linking moiety is attached to a vertex of said first polygon moiety and a vertex of said second polygon moiety; and wherein the faceted polyhedron molecule is a discrete macromolecule.

25. A faceted polyhedron molecule or polymeric structure comprising polygon moieties and linking moieties, wherein said polygon moieties comprise edges and vertices, wherein a first polygon moiety is attached to a second polygon moiety by at least one or said linking moieties, wherein said at least one linking moiety is attached to a vertex of said first polygon moiety and a vertex of said second polygon moiety; and wherein said faceted polymeric molecule or polymeric structure is $[(L)(S)Cu_2(bdc)_2]_{12}$ or $[(S) Cu_2(bdc)_2]_{12}$, wherein L is pyridine, S is methanol, and bdc is benzene-1,3-dicarboxylate.

26. A faceted polyhedron molecule or polymeric structure comprising polygon moieties and linking moieties, wherein said polygon moieties comprise edges and vertices, wherein a first polygon moiety attached to a second polygon moiety by at least one of said linking moieties, wherein said at least one linking moiety is attached to a vertex of said first polygon moiety and a vertex of said second polygon moiety, wherein said at least one linking moiety is a coordinating ligand or a bridging ligand, and wherein at least one of said first and second polygon moieties comprises a non-metal moiety and said linking moiety is a bridging ligand.

27. The faceted polyhedron molecule or polymeric structure of claim 26, wherein said bridging ligand is a multi-functional molecular moiety capable of sustaining multiple supramolecular interaction.

28. A faceted polyhedron molecule or polymeric structure comprising polygon moieties and linking moieties, wherein said polygon moieties comprise edges and vertices, wherein a first polygon moiety attached to a second polygon moiety by at least one of said linking moieties, wherein said at least one linking moiety is attached to a vertex of said first polygon moiety and a vertex of said second polygon moiety, and wherein said first polygon moiety comprises a non-metal and said second polygon moiety comprises a non-metal.

29. The faceted polyhedron molecule or polymeric structure of claim 28, wherein said first polygon moiety comprises a non-metal and second polygon moiety comprises a non-metal, wherein the vertices of said first and second polygon moieties are connected by a bridging ligand.

* * * * *

UNITED STATES PATENT AND TRADEMARK OFFICE
CERTIFICATE OF CORRECTION

PATENT NO.    : 6,965,026 B2
DATED         : November 15, 2005
INVENTOR(S)   : Michael J. Zaworotko and Brian Moulton It is certified that error appears in the above-identified patent and that said Letters Patent is hereby corrected as shown below:

Column 3,
Line 39, "subject,invention" should read -- subject invention --.

Column 5,
Line 44, "J = -350 c$^{-1}$ and" should read -- J = -350 cm$^{-1}$ and --.

Column 6,
Line 62, "carboxylate ii that" should read -- carboxylate that --.

Column 8,
Line 21, "criterion g include" should read -- criterion include --.
Line 55, "$(M^1_6A^1_5)_4$" should read -- $(M_{16}A_{15})_4$ --.

Column 9,
Line 9, "the nSBt" should read -- the nSBU --.

Column 12,
Line 6, "(1 mnmol)" should read -- (1 mmol) --.
Line 42, "1520 cm$^{-1}$," should read -- 1520 cm$^{-1}$ --.

Column 15,
Line 9, "$\{[XL_2Zn_2(btc),]$" should read -- $\{[XL_2Zn_2(btc)_1]$ --.

Column 16,
Line 16, "space group 14/mmm," should read -- space group I4/*mmm*, --.
Line 18, "-31≧k>31," should read -- -31≥$k$≥31, --.
Line 19, "-36≧I>21])." should read -- -31≥$l$≥21). --.

Column 17,
Line 50, "in 2⊖ and" should read -- in 2⊖ and --.

Column 20,
Line 32, "0.741 nmol)" should read -- 0.741 mmol --.

UNITED STATES PATENT AND TRADEMARK OFFICE
CERTIFICATE OF CORRECTION

PATENT NO. : 6,965,026 B2
DATED : November 15, 2005
INVENTOR(S) : Michael J. Zaworotko and Brian Moulton It is certified that error appears in the above-identified patent and that said Letters Patent is hereby corrected as shown below:

Column 22,
Line 35, "molecules" should read -- molecule --.
Line 39, "1-propanol" should read -- I-propanol --.
Line 55, "one or said" should read -- one of said --.

Signed and Sealed this

Fourth Day of April, 2006

JON W. DUDAS
*Director of the United States Patent and Trademark Office*